US012665090B2

(12) United States Patent
Rockne et al.

(10) Patent No.: US 12,665,090 B2
(45) Date of Patent: Jun. 23, 2026

(54) MACHINE LEARNING FOR HEALTHCARE SERVICE PLANNING

(71) Applicant: MatrixCare, Inc., Bloomington, MN (US)

(72) Inventors: Jessica Rockne, West Jordan, UT (US); Kedar Mangesh Kadam, Nova Scotia (CA)

(73) Assignee: MatrixCare, Inc., Bloomington, MN (US)

( * ) Notice: Subject to any disclaimer, the term of this patent is extended or adjusted under 35 U.S.C. 154(b) by 357 days.

(21) Appl. No.: 18/054,766

(22) Filed: Nov. 11, 2022

(65) Prior Publication Data

US 2024/0161929 A1 May 16, 2024

(51) Int. Cl.
*G16H 50/30* (2018.01)
*G06N 20/00* (2019.01)

(52) U.S. Cl.
CPC ............. *G16H 50/30* (2018.01); *G06N 20/00* (2019.01)

(58) Field of Classification Search
CPC ............................... G16H 50/30; G06N 20/00
See application file for complete search history.

(56) References Cited

U.S. PATENT DOCUMENTS

| | | | |
|---|---|---|---|
| 11,238,469 B1 * | 2/2022 | Talvola | G06N 20/20 |
| 11,417,418 B1 * | 8/2022 | Jain | H04L 41/147 |
| 11,664,097 B2 * | 5/2023 | Farooq | G06Q 10/10 |
| | | | 705/3 |
| 12,046,360 B2 * | 7/2024 | Kogan | G01C 21/3697 |
| 2021/0090695 A1 * | 3/2021 | Farooq | G16H 10/60 |

OTHER PUBLICATIONS

Zheng, Elsevier, 2015, pp. 7110-7120.*
Ghosh, Springer Feb. 2022, pp. 1-384.*

* cited by examiner

*Primary Examiner* — Michael I Ezewoko

(74) *Attorney, Agent, or Firm* — Patterson + Sheridan, LLP

(57) ABSTRACT

Techniques for improved machine learning are provided. User data describing one or more conditions of a user is received, and a healthcare service plan is generated for the user, comprising: extracting a plurality of user attributes, from the user data, for the user, selecting a first alternative healthcare service plan having a set of one or more home healthcare services to be provided to the user, and generating a predicted outcome score by inputting the first alternative healthcare service plan and the plurality of user attributes into a trained machine learning model. The healthcare service plan is implemented for the user based at least in part on the predicted outcome score.

17 Claims, 17 Drawing Sheets

100

105

110
User Attributes

120
Condition Data

130
Service Plans

135
Machine Learning System

140
Machine Learning Model

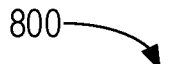
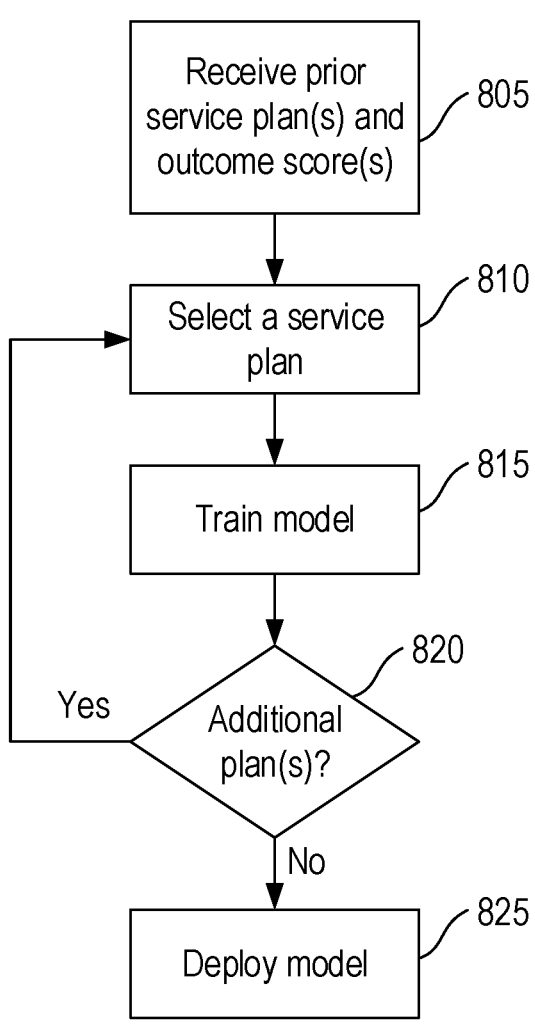
800
Receive prior
service plan(s) and
outcome score(s) ⎯ 805
Select a service
plan ⎯ 810
Train model ⎯ 815
Additional
plan(s)? ⎯ 820
Yes
No
Deploy model ⎯ 825
FIG. 8

900

905
Receive user data

910
Select a service plan

915
Extract user attributes

920
Identify selected service(s)

925
Determine hospitalization status

930
Determine time to hospitalization

935
Generate outcome score(s)

940
Additional plan(s)?

Yes

No

945
End

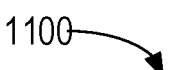
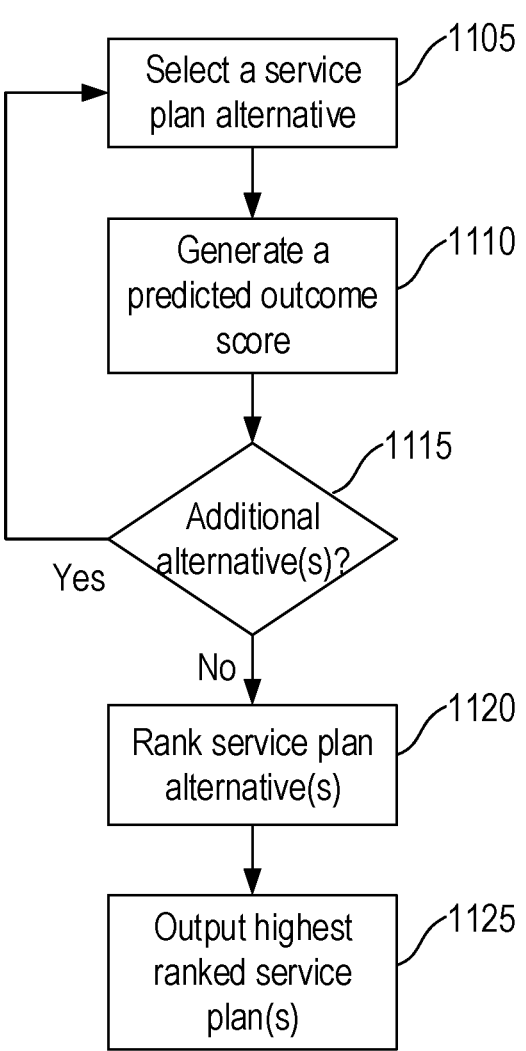
1100
Select a service plan alternative — 1105
Generate a predicted outcome score — 1110
Additional alternative(s)? — 1115
Yes
No
Rank service plan alternative(s) — 1120
Output highest ranked service plan(s) — 1125
*FIG. 11*

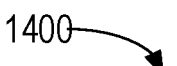
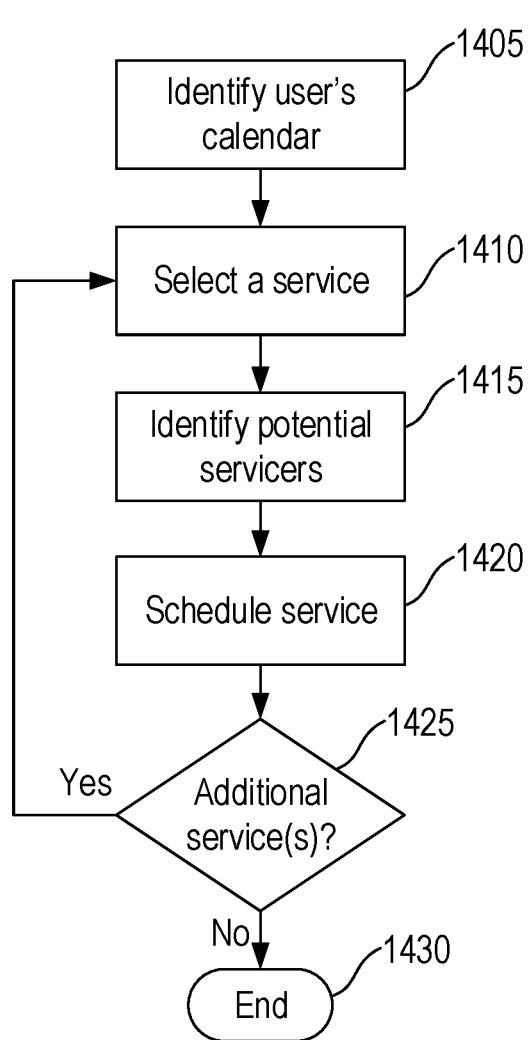
*FIG. 14*

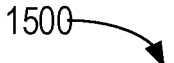

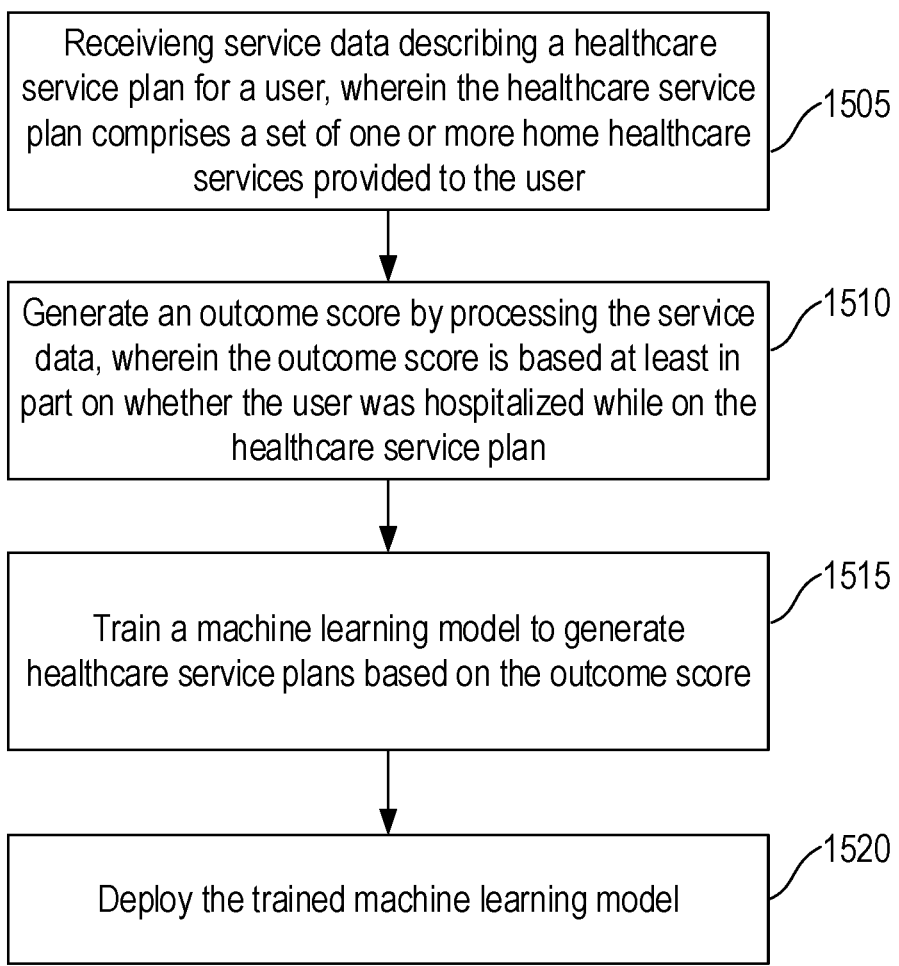

1500

Receivieng service data describing a healthcare service plan for a user, wherein the healthcare service plan comprises a set of one or more home healthcare services provided to the user ⟋1505

Generate an outcome score by processing the service data, wherein the outcome score is based at least in part on whether the user was hospitalized while on the healthcare service plan ⟋1510

Train a machine learning model to generate healthcare service plans based on the outcome score ⟋1515

Deploy the trained machine learning model ⟋1520

*FIG. 15*

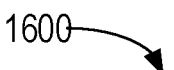

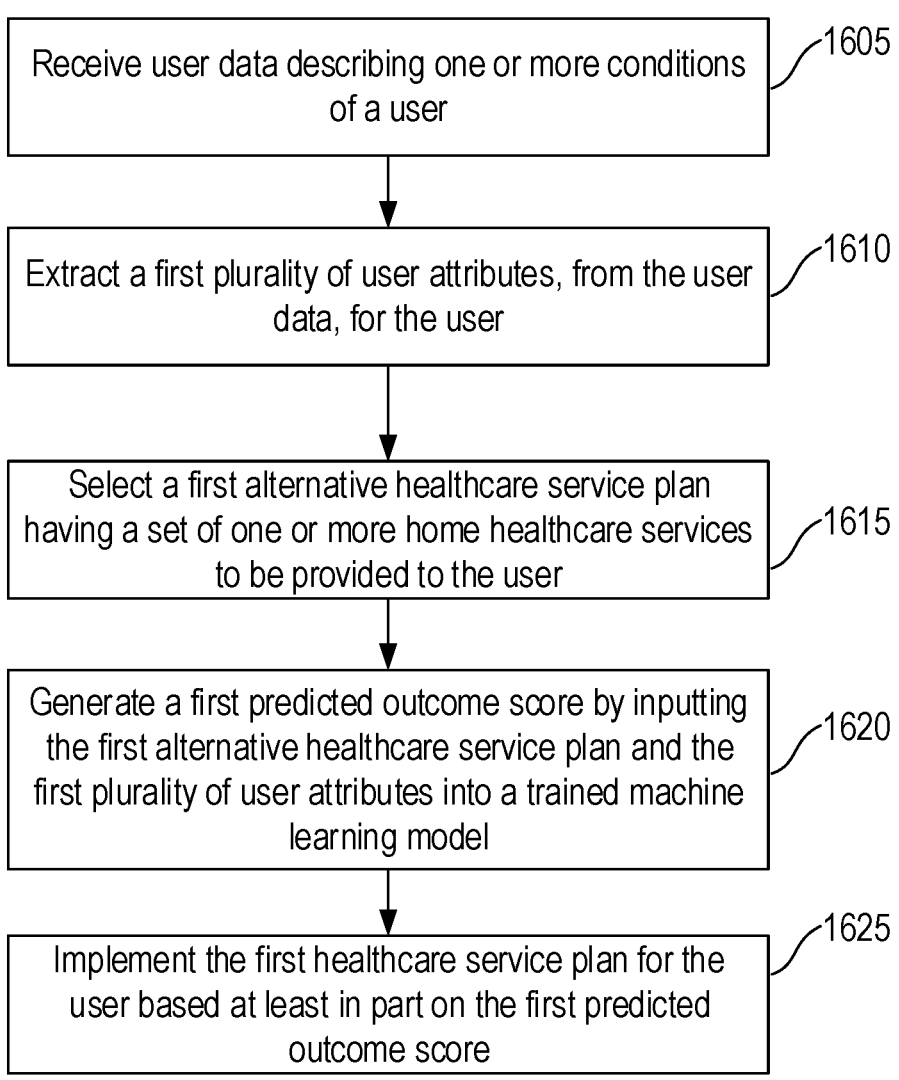

1600

Receive user data describing one or more conditions of a user   /1605

Extract a first plurality of user attributes, from the user data, for the user   /1610

Select a first alternative healthcare service plan having a set of one or more home healthcare services to be provided to the user   /1615

Generate a first predicted outcome score by inputting the first alternative healthcare service plan and the first plurality of user attributes into a trained machine learning model   /1620

Implement the first healthcare service plan for the user based at least in part on the first predicted outcome score   /1625

*FIG. 16*

MACHINE LEARNING FOR HEALTHCARE SERVICE PLANNING

INTRODUCTION

Embodiments of the present disclosure relate to machine learning. More specifically, embodiments of the present disclosure relate to using machine learning to generate and evaluate home service plans in healthcare settings.

In many healthcare settings, such as in residential care facilities (e.g., nursing homes) or in-home care settings (e.g., where users or patients receive healthcare services while residing in their own homes), a wide variety of user, patient, or resident characteristics are assessed and monitored in an effort to reduce or prevent worsening any resident's condition. Additionally, various service plans are often devised by clinicians or other healthcare providers in an effort to ameliorate any issues or concerns for the user. For example, service plans may be used to ensure that the user is able to remain at home safely (e.g., as opposed to being admitted to a hospital or nursing home). However, such service plans have a multitude of varying alternatives and options, and are tremendously complex to design. Without appropriate service planning, these problems can lead to clinically significant negative outcomes and complications.

Conventionally, healthcare providers (e.g., doctors, nurses, caregivers, and the like) strive to provide adequate healthcare service planning using manual assessments (e.g., relying on subjective experience). However, such conventional approaches are entirely subjective (relying on the expertise of individual caregiver to recognize and care for possible concerns), and frequently fail to identify the most optimal service plans for a variety of users. Further, given the vast complexity involved in these plans, it is simply impossible for healthcare providers to evaluate all relevant data and alternatives in order to select optimal plans.

Improved systems and techniques to automatically generate and/or evaluate service plans are needed.

SUMMARY

According to one embodiment presented in this disclosure, a method is provided. The method includes: receiving user data describing one or more conditions of a user; generating a first healthcare service plan for the user, comprising: extracting a first plurality of user attributes, from the user data, for the user; selecting a first alternative healthcare service plan having a set of one or more home healthcare services to be provided to the user; and generating a first predicted outcome score by inputting the first alternative healthcare service plan and the first plurality of user attributes into a trained machine learning model; and implementing the first healthcare service plan for the user based at least in part on the first predicted outcome score.

According to one embodiment presented in this disclosure, a method is provided. The method includes: receiving user data describing one or more conditions of a user; generating a first healthcare service plan for the user, comprising: extracting a first plurality of user attributes, from the user data, for the user; selecting a first alternative healthcare service plan having a set of one or more home healthcare services to be provided to the user; and generating a first predicted outcome score by inputting the first alternative healthcare service plan and the first plurality of user attributes into a trained machine learning model; and implementing the first healthcare service plan for the user based at least in part on the first predicted outcome score.

Other embodiments presented in this disclosure provide processing systems configured to perform the aforementioned methods as well as those described herein; non-transitory, computer-readable media comprising instructions that, when executed by a processor of a processing system, cause the processing system to perform the aforementioned methods as well as those described herein; a computer program product embodied on a computer-readable storage medium comprising code for performing the aforementioned methods as well as those further described herein; and a processing system comprising means for performing the aforementioned methods as well as those further described herein.

The following description and the related drawings set forth in detail certain illustrative features of one or more embodiments.

DESCRIPTION OF THE DRAWINGS

The appended figures depict certain aspects of the one or more embodiments and are therefore not to be considered limiting of the scope of this disclosure.

FIG. 8 is a flow diagram depicting an example method for training machine learning models to generate and evaluate service plans.

FIG. 11 is a flow diagram depicting an example method for generating and evaluating service plan alternatives using machine learning.

FIG. 14 is a flow diagram depicting an example method for automatically implementing service plans.

FIG. 15 is a flow diagram depicting an example method for training machine learning models to improve service planning.

FIG. 16 is a flow diagram depicting an example method for generating and evaluating service plans using trained machine learning models.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1:
FIG. 1 depicts an example workflow for training machine learning models based on historical data.

Aspects of the present disclosure provide apparatuses, methods, processing systems, and computer-readable mediums for improved machine learning to generate and evaluate healthcare service plans, such as for at-home care.

In some embodiments, a machine learning model (also referred to in some aspects as a service model or an outcome model) can be trained and used as a tool for clinicians (e.g., nurses, caregivers, doctors, and the like) to assist in generating and evaluating healthcare service plans for users (e.g., patients, residents of a long-term care facility, and the like), thereby improving care, and preventing potentially significant negative outcomes. In some embodiments, by monitoring for changes in the conditions for each user, the system is able to identify those in need of revised service plans, and can assist with reallocating resources and driving targeted interventions to help mitigate, prevent, or reduce the effect of a myriad of problems and disorders.

In some aspects, machine learning is used to evaluate service plans with the goal that the user can reside or remain in their own home, with the assistance of one or more services to prevent or reduce harm to the user and ensure their safety. The services included in a given service plan may vary substantially depending on the particular needs of the user. For example, a service plan may include use of an emergency call button (e.g., a worn device that summons help with a single press of a button), remote monitoring (e.g., allowing a healthcare provider to check-in on the user), dietician assistance (e.g., where a dietician or other provider assists with meal planning and/or consumption), home modifications (e.g., installation of ramps, handrails, and/or lifts), therapies (e.g., physical therapy), in-home assistance (e.g., to help clean or bathe), and the like.

In some embodiments, the machine learning models generate and/or score service plans for one or more targets or goals, such as reduced probability of hospitalization. That is, a machine learning model may be trained to score a plan, with respect to an individual user, based on the probability that the plan will enable the user to reside at home without the need to be transferred to a residential facility or hospital. In some aspects, other goals may additionally or alternatively be used.

In conventional settings, care providers must rely on subjective assessments and plans (e.g., manually selecting service plans) to assist users. In addition to this inherently subjective and inaccurate approach, many conventional systems are largely static and have difficultly responding to dynamic situations (e.g., changing user conditions) which are common in practice. Moreover, the vast number and variety of alternative services that can be used (and the various degrees or types of services within each alternative service), as well as the significant amounts of data available for each user, render accurate analysis and selection of proper plans impossible to adequately perform manually or mentally. Aspects of the present disclosure can not only reduce or prevent this subjective review, but can further prevent wasted time and computational expense spent reviewing vast amounts of irrelevant data and sub-optimal plans. Further, aspects of the present disclosure enable more accurate evaluations, more efficient use of computational and other resources (e.g., reducing or eliminating frequent requests for information, and efficiently evaluating vast stores of data), and overall improved outcomes for users (e.g., through reduced harm to the user and/or reduced re-hospitalization).

Embodiments of the present disclosure can generally enable proactive and quality care for users, as well as dynamic and targeted interventions, that help to prevent or reduce adverse events due to a variety of issues and conditions. This autonomous and continuous updating based on changing conditions with respect to individual users enables a wide variety of improved results, including not only improved outcomes for the users (e.g., reduced negative outcomes, early identification of optimal plans, targeted interventions, and the like) but also improved computational efficiency and accuracy of the evaluation and solution process.

In some embodiments, a variety of historical user data can be collected and evaluated to train one or more machine learning models. During such training, the machine learning model(s) can learn a set of features (e.g., user attributes) and/or a set of weights for such features. These features and weights can then be used to automatically and efficiently process new user data in order to generate and evaluate improved service plans. For example, the system may, using a relatively large number of exemplars from prior service plans, learn which set(s) or combinations of services worked to reduce or prevent adverse events (e.g., re-hospitalization) based on the individual user's attributes (e.g., their diagnoses, status, and the like). When a new service plan is needed for a user, the model can be used to identify or suggest an optimal combination of services to ensure they can safely reside in their home.

In some aspects, the model may be trained during a training phase, and then be deployed as a static model that, once deployed, remains fixed. In other embodiments, the model may be refined or updated (either periodically or upon specified criteria). That is, during use in evaluating and generating in potential plans, the model may be refined based on feedback from users, caregivers, and the like. For example, if a clinician indicates that a service plan was successful in preventing hospitalization (regardless of whether the model suggested the plan), the model may be refined based on this indication. Similarly, if a clinician indicates that a service plan failed to prevent hospitalization, the model may be refined to reflect this new data.

Example Workflow for Training Machine Learning Models Using Historical Data

FIG. 1 depicts an example workflow 100 for training machine learning models based on historical data.

In the illustrated workflow 100, a set of historical data 105 is evaluated by a machine learning system 135 to generate one or more machine learning models 140. In embodiments, the machine learning system 135 may be implemented using hardware, software, or a combination of hardware and software. The historical data 105 generally includes data or information associated with one or more users (also referred to as residents or patients) from one or more prior points in time. That is, the historical data 105 may include, for one or more users, a set of one or more snapshots of the user's characteristics or attributes at one or more points in time. For example, the historical data 105 may include attributes for a set of users that receive in-home care (e.g., one or more healthcare services in their own home). In some embodiments, the historical data 105 includes indications of when any of the user attributes changed (e.g., records indicating the updated attributes whenever a change occurs). The historical data 105 may generally be stored in any suitable location. For example, the historical data 105 may be stored within the machine learning system 135, or may be stored in one or more remote repositories, such as in a cloud storage system.

In the illustrated example, the historical data 105 includes, for each user reflected in the data, a set of one or more user attributes 110, condition data 120, and service plans 130. In some embodiments, as discussed above, the historical data 105 includes data at multiple points in time for each user. That is, for a given user, the historical data 105 may include multiple sets of user attributes 110 (one set for each relevant point in time), and the like. In some embodiments, the user attributes 110, condition data 120, and/or service plans 130 can be linked or associated (e.g., using timestamps or other indications of the relevant time or period) for the data. That is, the machine learning system 135 may be able to identify the relevant data for any given point or window of time. For example, for a given service plan 130 at a given time, the machine learning system 135 can identify all the relevant data surrounding this time (e.g., the user attributes 110 and/or condition data 120 at the time the plan was instantiated, within a predefined window before the time, such as one month prior, and the like).

In some aspects of the present disclosure, the various components of the historical data 105 are described with reference to a single user for conceptual clarity (e.g., user attributes 110 of a single user) and/or for a single time (e.g., a single service plan 130 for the user). However, it is to be understood that the historical data 105 can generally include such data for any number of users and times.

As discussed in more detail below, the user attributes 110 generally correspond to a set of one or more specified features, attributes, or characteristics describing the user(s). For example, the user attributes 110 may include characteristics such as the user's age, diagnoses or disorders they have, and the like. In at least one embodiment, the user attributes 110 can include information or data generated by machine learning models. For example, the user attributes 110 may include a fall risk score indicating a probability that the user will fall and/or a predicted severity of such a fall (generated by one or more trained models based on various user data), an acuity score indicating the acuity or degree of care needed by the user (generated by one or more trained models based on various user data), a depression risk score indicating a probability that the user has or will develop depression (generated by one or more trained models based on various user data), and the like.

In some embodiments, the user attributes 110 are curated or selected based on their impact on what services are needed by the user. For example, in one aspect, a user (e.g., a clinician) may manually specify attributes that have a high impact on service plan success and/or which services are needed. In some embodiments, some or all of the attributes may be inferred or learned (e.g., using one or more feature selection techniques). For example, one or more machine learning models or feature selection algorithms may be used to identify specific attributes (or to determine dynamic weights for each attribute).

As discussed in more detail below, the condition data 120 generally corresponds to information relating to the state or condition of the user. For example, the condition data 120 may indicate, for one or more points or windows of time, whether the user is hospitalized (as of the time associated with the data) or otherwise in a care facility. By using the condition data 120, the machine learning system 135 can correlate service plans 130 and user attributes 110 with resulting outcomes (e.g., hospitalizations) to identify an ideal set of services for given users.

As discussed in more detail below, the service plans 130 can generally indicate a set of details for services (e.g., in-home services) that are received by the user. Each service plan 130 can generally include any number and variety of services (as well as any variety of intensities or levels of each such service) for the user at any given point in time. For example, a given service plan 130 may indicate that the corresponding user received in-home dietician assistance during a given window of time. Example healthcare services that may be indicated in a service plan 130 may include, without limitation, home modifications (e.g., installation of safety devices such as handrails or chairlifts, medical equipment, rearranging of furniture, widening of doorways, and the like), remote monitoring services (e.g., use of cameras, microphones, or other sensors to allow clinicians or others to check in with users, such as to collect vital signs, temperature, blood pressure, heart rates, and the like), emergency call equipment (e.g., a stationary, portable, and/or wearable device including a button or other input allowing the user to quickly request emergency assistance), dietician assistance (e.g., a dietician that assists with planning and/or preparing meals for the user), one or more therapies (e.g., physical therapy and/or mental health therapy), in-home assistance from a healthcare provider or other provider (e.g., a nurse practitioner who provides assistance, or a cleaning service), and the like.

As additional examples of healthcare services, the service plan 130 may include elements such as occupational therapy, speech and language pathology, personal care aide(s), housekeeper(s), social work, spiritual support, physician support, and the like. Additionally, the plans may include performing personal services such as completing advanced directives, living wills, power or attorney, and/or services such as labs/blood draws by a nurse or phlebotomist, medication reconciliation by a pharmacist, non-medical transportation arrangements, mobile imaging (e.g., x-rays), nebulizer treatments, IVs (antibiotics or other), and the like.

In some embodiments, some or all of the service plans 130 are crafted by clinicians (e.g., nurses or doctors) for the user. That is, the service plans 130 may represent historical plans that were defined for users to enable them to reside in their homes (as opposed to requiring hospitalization or admission to a residential care facility). As discussed below in more detail, the machine learning system 135 can generally evaluate these historical service plans 130 to determine how effective they were (e.g., whether the user was able to remain at home or was hospitalized or admitted to a facility, how much time elapsed before an admission to a facility, and the like). One or more machine learning models 140 can then be trained to generate and/or score new service plans to indicate whether they should be used for a given user (e.g., how likely they are to prevent hospitalization, and the like) based on the user's attributes.

Although the illustrated historical data 105 includes several specific components including user attributes 110, condition data 120, and service plans 130, in some embodiments, the historical data 105 used by the machine learning system 135 may include fewer components (e.g., a subset of the illustrated examples) or additional components not depicted. Additionally, though the illustrated example provides general groupings of data to aid understanding, in some embodiments, the historical data 105 may be represented using any number of groups. For example, the condition data 120 may be reflected in the user attributes 110.

As illustrated, the machine learning system 135 generates one or more machine learning models 140 based on the historical data 105. The machine learning model 140 generally specifies a set of weights for the various features or attributes of the historical data 105. In some embodiments, the machine learning model 140 specifies weights specifically for each individual feature (e.g., for each attribute in the set of attributes 110). For example, a first attribute may be associated with a lower weight than a second attribute. Similarly, in some embodiments, the machine learning model 140 specifies different weights depending on the severity of the feature (e.g., depending on the severity of a disorder or diagnosis).

In some embodiments, during a training phase, the machine learning system 135 may process the historical data 105 for a given user at a given time as input to the machine learning model 140 (along with the service plan 130 used by the user at the time) in order to generate a predicted outcome or efficacy of the service plan (e.g., indicating the probability that the user will require hospitalization). The machine learning system 135 can then compare the generated probability to a ground-truth (e.g., data in the condition data 120 indicating whether the user was admitted to a hospital). The difference between the generated and actual scores can be used to refine the weights of the machine learning model 140, and the model can be iteratively refined (e.g., using data from multiple users and/or multiple points in time) to accurately evaluate service plans.

In some embodiments, during or after training, the machine learning system 135 may prune the machine learning model 140 based in part on the learned weights. For example, if the learned weight for a given feature (e.g., a specific user attribute 110) is below some threshold (e.g., within a threshold distance from zero), the machine learning system 135 may determine that the feature has no impact (or negligible impact) on the success of service plans. Based on this determination, the machine learning system 135 may cull or remove this feature from the machine learning model 140 (e.g., by removing one or more neurons, in the case of a neural network). For future evaluations, the machine learning system 135 need not receive data relating to these removed features (and may refrain from processing or evaluating the data if it is received). In this way, the machine learning model 140 can be used more efficiently (e.g., with reduced computational expense and latency) to yield accurate evaluations.

In some embodiments, the machine learning system 135 can generate multiple machine learning models 140. For example, a separate machine learning model 140 may be generated for each region (e.g., with a unique model for each country). This may allow the machine learning system 135 to account for facility-specific, region-specific, or culture-specific changes (e.g., due to climate, average sunlight, and the like). In other embodiments, the machine learning system 135 generates a universal machine learning model 140. In at least one embodiment, a global machine learning model 140 may use similar considerations (e.g., location, region, and the like) as an input feature.

In some embodiments, the machine learning system 135 outputs the machine learning model 140 to one or more other systems for use. That is, the machine learning system 135 may distribute the machine learning model 140 to one or more downstream systems, where each downstream system is used to generate service plans. For example, the machine learning system 135 may deploy the machine learning model 140 to one or more servers associated with specific facilities or care providers, and these servers may use the model to evaluate potential service plans for users or patients. In at least one embodiment, the machine learning system 135 can itself use the machine learning model to evaluate service plans.

Example Workflow for Generating Training Data for Machine Learning

Figure 2:
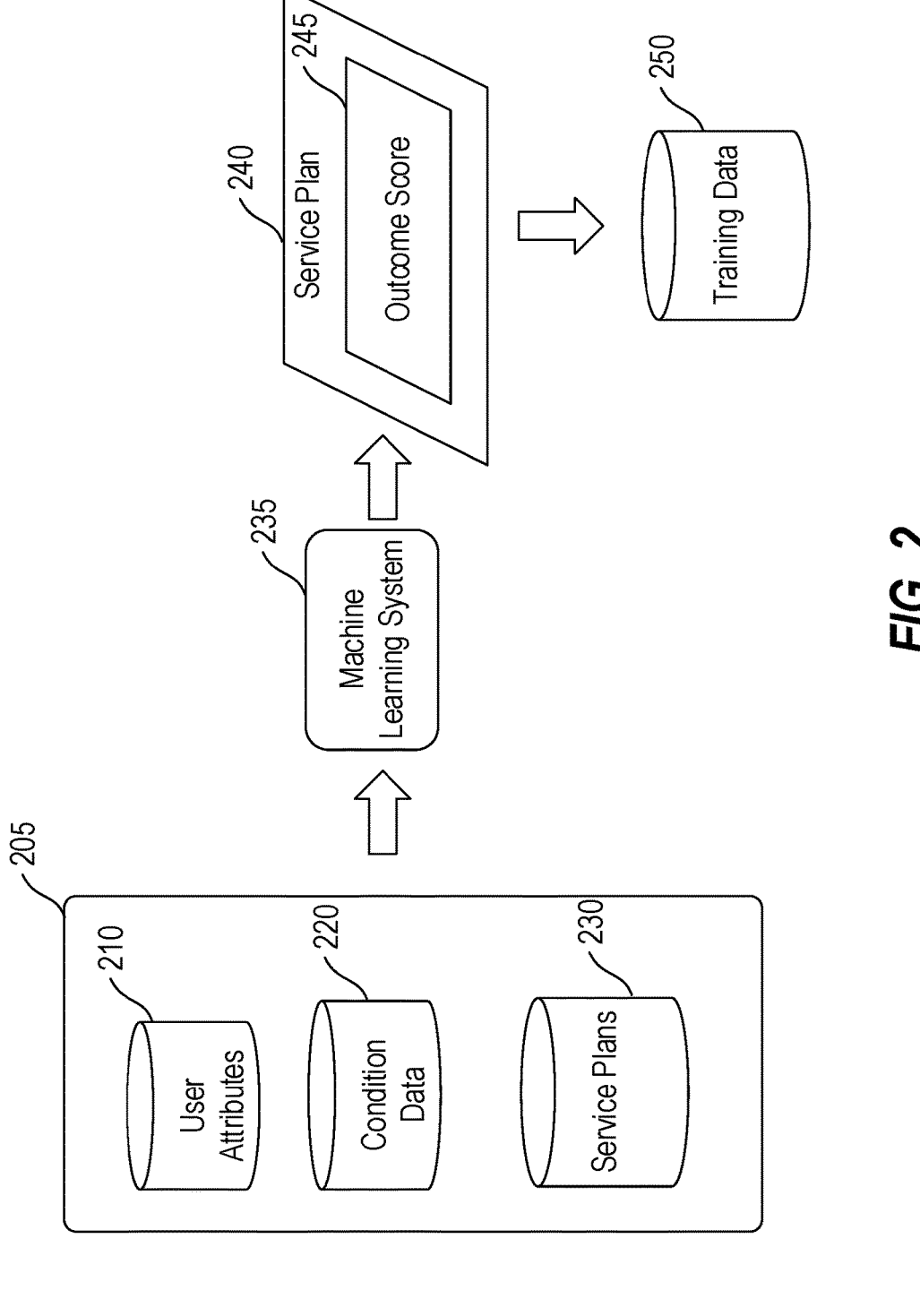
FIG. 2 depicts an example workflow for generating training data to drive improved service planning.

FIG. 2 depicts an example workflow 200 for generating training data to drive improved service planning. In some embodiments, the workflow 200 is used to generate the training data used to train machine learning models (e.g., using the workflow 100 of FIG. 1).

In the illustrated workflow 200, a set of historical data 205 is evaluated by a machine learning system 235 to generate outcome scores 245 for prior service plans 240, which are used to form training data 250. This training data 250 can then be used to train one or more machine learning models, such as machine learning model 140 of FIG. 1.

In embodiments, the machine learning system 235 may be implemented using hardware, software, or a combination of hardware and software. In some embodiments, the machine learning system 235 corresponds to the machine learning system 135 of FIG. 1. That is, the same machine learning system may both generate training data 250, and use it to train models. In other embodiments, one or more systems may generate the training data 250, while one or more other systems use the training data 250 to train models.

The historical data 205 generally includes data or information associated with one or more users (also referred to as residents or patients) from one or more prior points in time, as discussed above. In the illustrated example, as discussed above, the historical data 205 includes, for each user reflected in the data, a set of one or more user attributes 210, condition data 220, and service plans 230 at one or more points in time.

As discussed above, the user attributes 210 generally correspond to a set of one or more specified features, attributes, or characteristics describing the user(s) (such as fall risk, depression risk, acuity score, demographic data, and the like), the condition data 220 generally corresponds to information relating to whether the user is (or has been) admitted to a care facility or hospital, and the service plans 230 can generally indicate a set of services provided to the user (e.g., in-home healthcare services). As discussed above, the service plans 230 may have been crafted by clinicians (e.g., nurses or doctors) for the user. That is, the service plans 230 may represent historical plans that were defined to allow the user to reside at home.

Although the illustrated historical data 205 includes several specific components including user attributes 210, condition data 220, and service plans 230, in some embodiments, the historical data 205 used by the machine learning system 235 may include fewer components (e.g., a subset of the illustrated examples) or additional components not depicted. Additionally, though the illustrated example provides general groupings of data to aid understanding, in some embodiments, the historical data 205 may be represented using any number of groups. For example, the condition data 220 may be reflected in the user attributes 210.

In the illustrated workflow 200, the machine learning system 235 can generally evaluate these historical service plans 230 to determine how effective they were (e.g., whether they allowed the user to remain at home, as opposed to being admitted to a care facility, how long the user was able to remain at home before such admission, and the like) in order to generate, for each respective service plan, a corresponding outcome score 245. In some embodiments, the outcome score 245 is one or more numerical values indicating the efficacy of a specific service plan 240 for a specific user. For example, the outcome score 245 may indicate a probability that the service plan 240 will (or did) allow the user to remain safely at home.

As illustrated, the outcome score 245 is used to create a training exemplar 240 including the corresponding service plan. In an embodiment, the exemplar 240 also includes the relevant user attributes 210 (which may include other conditions of the user). That is, the exemplar 240 can indicate the user attributes 210 at a given time or window of time (e.g., just before the service plan 230 was generated, during use of the service plan, and the like). This data can be used as input to train the model, while the determined outcome score 245 is used as target output. In some embodiments, the exemplar 240 also includes the specifics of the service plan. That is, the model may be trained to receive, as input, indications as to which service(s) are included in the plan, alongside the user attributes. This can allow the model to predict the probability of success for a given plan, given the user attributes.

By comparing the actual outcome score 245 (e.g., defined based on whether the user was admitted to a hospital or other facility) to the score generated by the machine learning model, the machine learning system can iteratively refine the model to generate more accurate outcome scores.

In at least one embodiment, the training data 250 can be used to train multiple models. For example, a first model may be trained to predict whether a user is likely to be re-hospitalized or otherwise admitted to a facility. A second model may be trained to predict how much time will elapse before such admission (e.g., how long the user will be able to remain at home). In this way, the machine learning system can use the first model to select an ideal service plan for the user, while the second model is optionally used to predict how long the selected plan will work. In at least one aspect, the time-prediction model is used only if the service plan model predicts that the user is sufficiently likely to need hospitalization (e.g., above a threshold, or where the service plan outcome score is below a threshold). This can enable reduced computational resources as the second model is only selectively used.

Example Workflow for Generating Service Plans Using Machine Learning

Figure 3:
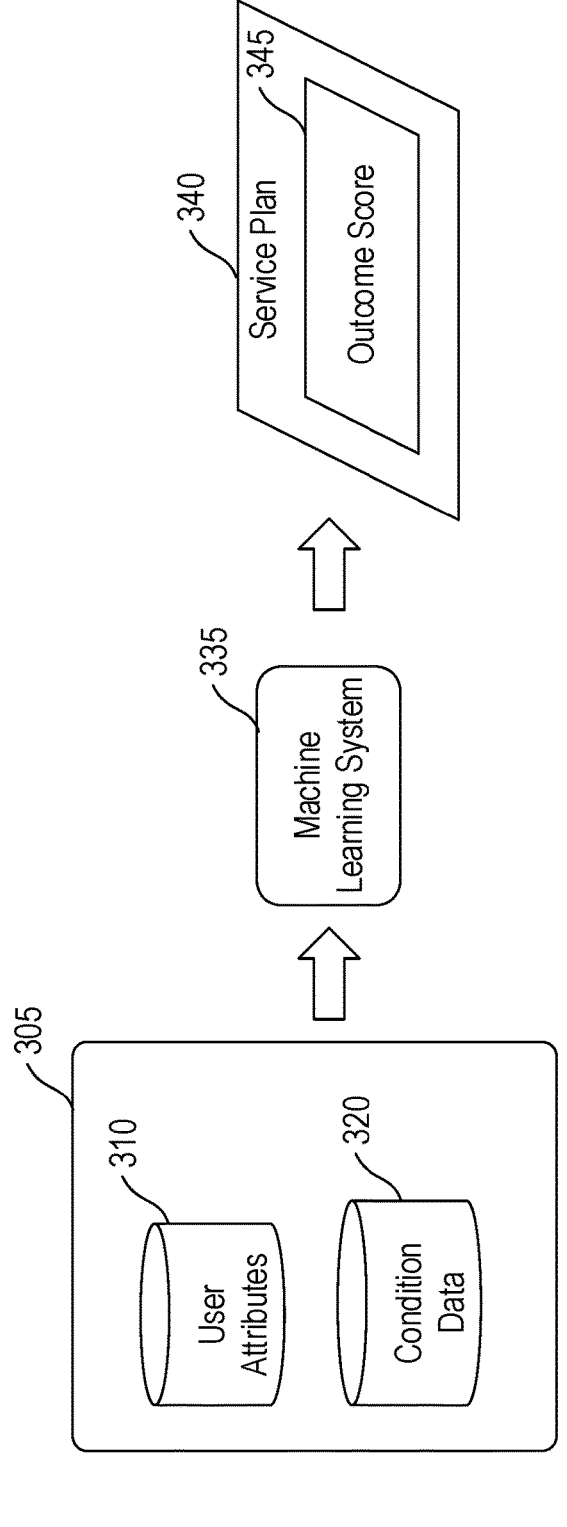
FIG. 3 depicts an example workflow for generating service plans and outcome scores using machine learning models.

FIG. 3 depicts an example workflow 300 for generating service plans and outcome scores using machine learning models. In some embodiments, the workflow 300 is performed using trained models, such as the machine learning models 140 of FIG. 1.

In the illustrated workflow 300, a set of user data 305 is evaluated by a machine learning system 335 using one or more machine learning models (e.g., machine learning model 140 of FIG. 1) to generate and/or evaluate one or more service plan(s) 340, each with a corresponding outcome score 345. In embodiments, the machine learning system 335 may be implemented using hardware, software, or a combination of hardware and software. In some embodiments, the machine learning system 335 corresponds to the machine learning system 135 of FIG. 1, and/or the machine learning system 235 of FIG. 2. In other aspects, as discussed above, the machine learning system 335 may differ from the system that trained the model and/or generated the training data.

The user data 305 generally includes data or information associated with one or more users, as discussed above. That is, the user data 305 may include, for one or more users, a set of one or more snapshots of their characteristics or attributes at one or more points in time. In the illustrated example, the user data 305 includes, for each user reflected in the data, a set of one or more user attributes 310 and condition data 320.

In some aspects, the user data 305 is selected or identified for processing based on determining that the corresponding user may benefit from a service plan 340. That is, based on determining that a service plan 340 that would allow a given user to remain at home may be more beneficial than treating the user in a facility (e.g., in a hospital or other care setting), the machine learning system 335 may determine to access and process the user data 305 to generate a plan. In at least one embodiment, to determine whether to use the machine learning model to process user data 305 for a given user, the machine learning system 335 (or a user of the machine learning system 335, such as a physician) can evaluate one or more aspects of the user data 305 using a form or rules-based evaluation.

For example, in one embodiment, the machine learning system 335 (or a user) may use a form or set of rules specifying certain conditions, attributes, or other factors that indicate whether the user should even be considered for at-home care. In one such embodiment, after entering the user's relevant information (e.g., indicating whether the user has one or more conditions), the form can indicate whether the user should be considered for at-home care, or if they cannot adequately be cared for at home (e.g., due to an inability to walk unassisted). In some embodiments, a care provider can use the form to identify relevant user(s) who satisfy the rule(s), and cause the machine learning system 335 to process these specific user's data to generate corresponding care plans 340. In other aspects, the machine learning system 335 may automatically identify potentially-eligible users. By using the machine learning model to evaluate only a subset of users (e.g., those that may be eligible for or benefit from at-home care), the machine learning system 335 can reduce the computational expense of the workflow 300.

As discussed above, the user attributes 310 generally include information relating to a set of one or more specified features, attributes, or characteristics describing the user(s) (such as fall risk, depression risk, acuity score, demographic data, and the like), and the condition data 320 generally indicates whether the user is currently hospitalized or otherwise admitted to or residing in a facility.

Although the illustrated user data 305 includes several discrete components for conceptual clarity, in some embodiments, the user data 305 used by the machine learning system 335 may include fewer components (e.g., a subset of the illustrated examples) or additional components not depicted. For example, the machine learning system 335 may evaluate only the user attributes 310, and not consider condition data 320.

In the illustrated example, the user data 305 is used to generate one or more service plans 340, each with a corresponding outcome score 345. As discussed above, the service plans 340 can generally indicate a set of services (e.g., in-home healthcare services) to be provided to the user. In at least one embodiment, the machine learning system 335 generates the service plans 340 and outcome scores 345 by processing a variety of alternatives (sequentially or in parallel). For example, for each alternative set of services, the machine learning system 335 may generate a corresponding score indicating the probability that the specific set of services will prevent readmission. These score(s) can then be used to define the outcome score 345 for each alternative service plan 340.

As discussed above, the machine learning system 335 can generate the outcome scores 345 by identifying or extracting the relevant attributes from the user data 305 (e.g., the relevant diagnoses, as indicated by the machine learning model), receiving an indication of the proposed service plan (e.g., the proposed set of services), and processing these attributes using the weights and architecture of the machine learning model to generate an overall outcome score 345 for the user based on the attributes and plan. In some embodiments, the outcome scores 345 can additionally or alternatively include a classification or category, such as a low, moderate, or high probability of success, or a short-term, medium-term, or long-term expected duration of the service plan, determined based on one or more threshold values for the outcome scores.

In at least one embodiment, the alternative plans can be ranked and/or filtered based on the outcome scores 345, and one or more top-scored service plans 340 can be selected. These top plans may be suggested or recommended to a user (e.g., output to a clinician via a graphical user interface (GUI)), automatically initiated, and the like.

In some embodiments, the machine learning system 335 can generate a new outcome score 345 and/or service plan 340 for each user periodically (e.g., weekly). In some embodiments, the machine learning system 335 generates a new service plan 340 and outcome score 345 whenever new data becomes available (or when the user data 305 changes). For example, when a new diagnosis is reported for a user, the machine learning system 335 may automatically detect the change and generate an updated service plan 340 that is specifically-tailored to the individual user at the specific time. This targeted prophylactic treatment can significantly improve user conditions and reduce harm (including the harm caused by admission to a facility).

Advantageously, the automatically generated service plans 340 and outcome scores 345 can significantly improve the outcomes of the users, helping to identify optimal plans, thereby preventing re-admission, preventing further deterioration, and significantly reducing harm. Additionally, the autonomous nature of the machine learning system 335 enables improved computational efficiency and accuracy, as the outcome scores 345 and/or service plans 340 are generated objectively (as opposed to the subjective judgment of clinicians or other users), as well as quickly and with minimal computational expense. That is, as the scores and plans can be automatically updated whenever new data is available, users need not manually retrieve and review the relevant data (which incurs wasted computational expense, as well as wasted time for the user).

Further, in some embodiments, the machine learning system 335 can regenerate service plans 340 and/or outcome scores 345 during specified times (e.g., off-peak hours, such as overnight) to provide improved load balancing on the underlying computational systems. For example, rather than requiring service providers to retrieve and review user data to determine if anything occurred or changed (which may require a new service plan), the machine learning system 335 can automatically identify such changes, and use the machine learning model(s) to regenerate service plans 340 and outcome scores 345. This can transfer the computational burden, which may include both processing power of the storage repositories and access terminals, as well as bandwidth over one or more networks, to off-peak times, thereby reducing congestion on the system during ordinary (e.g., daytime) use and taking advantage of extra resources that are available during the non-peak (e.g., overnight) hours.

In these ways, embodiments of the present disclosure can significantly improve user outcomes while simultaneously improving the operations of the computers and/or networks themselves (at least through improved and more accurate scores and plans, as well as better load balancing of the computational burdens).

Example Workflow for Refining Machine Learning Models

Figure 4:
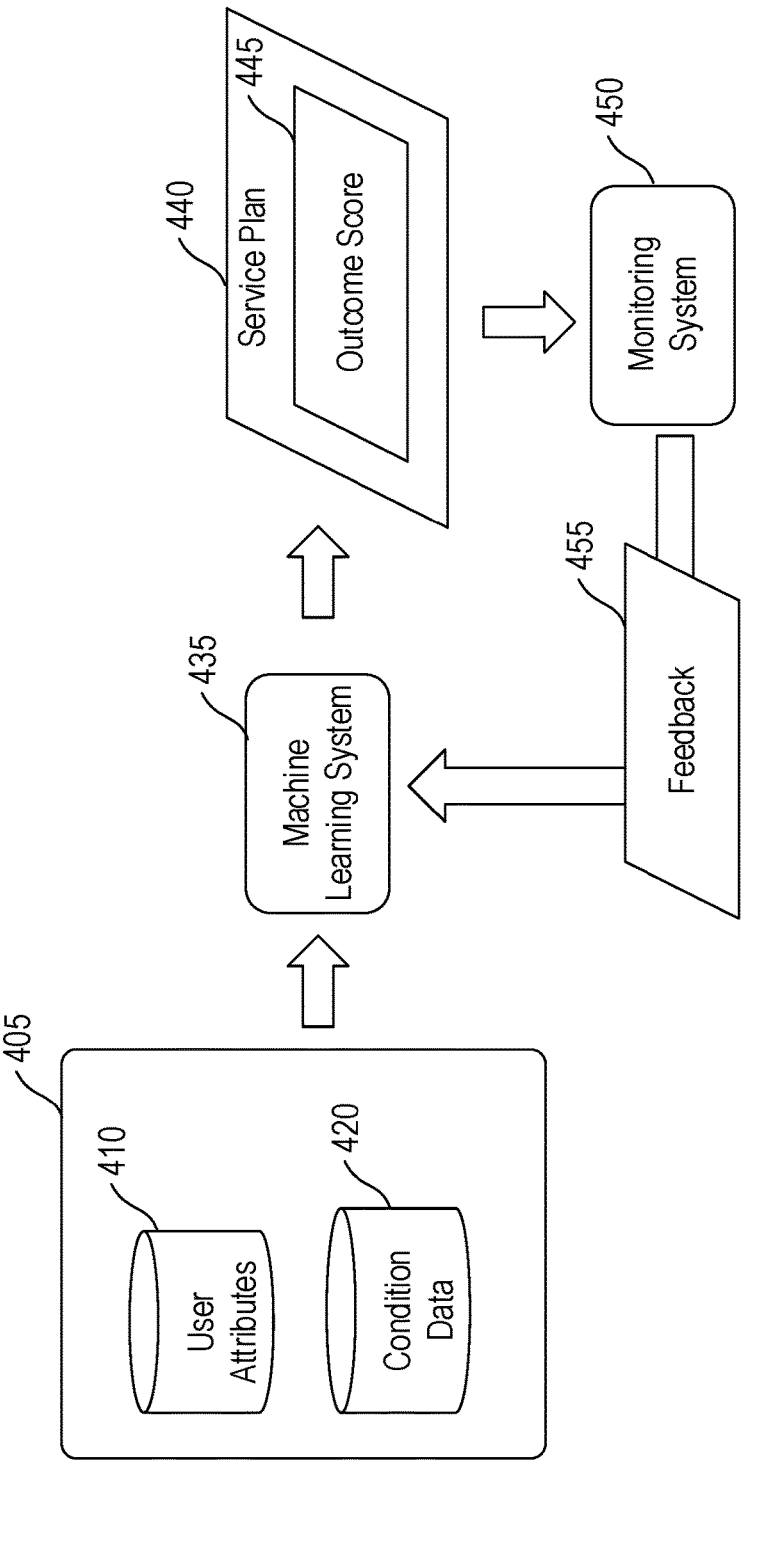
FIG. 4 depicts an example workflow for refining machine learning models to generate and evaluate service plans based on feedback mechanisms.

FIG. 4 depicts an example workflow 400 for refining machine learning models to generate and evaluate service plans based on feedback mechanisms. In some embodiments, the workflow 400 is performed using trained models, such as the machine learning models 140 of FIG. 1.

The depicted workflow 400 differs from the workflow 300 of FIG. 3 in that it enables online refinement of the machine learning models based on updated information, thereby ensuring that the models can dynamically create optimized plans even when general conditions change. In the illustrated workflow 400, a set of user data 405 is evaluated by a machine learning system 435 using one or more machine learning models (e.g., machine learning model 140 of FIG. 1) to generate and/or evaluate one or more service plan(s) 440, each with a corresponding outcome score 445. In embodiments, the machine learning system 435 may be implemented using hardware, software, or a combination of hardware and software. In some embodiments, the machine learning system 435 corresponds to the machine learning system 135 of FIG. 1, the machine learning system 235 of FIG. 2, the machine learning system 335 of FIG. 3. In other aspects, as discussed above, the machine learning system 435 may differ from the system that trained the model and/or generated the training data.

In some embodiments, the workflow 400 generally mirrors the workflow 300 of FIG. 3 to generate the service plans 440 and outcome scores 445. As discussed above, the user data 405 generally includes data or information associated with one or more users (also referred to as patients or residents). As discussed above, the user data 405 may include information for all users, or for a subset of users (e.g., users identified as potentially eligible for at-home care, which may be determined using a rules-based form or other techniques). In the illustrated example, the user data 405 includes, for each user reflected in the data, a set of one or more user attributes 410 and/or condition data 420. As discussed above, the user attributes 410 generally include information relating to a set of one or more specified features, attributes, or characteristics describing the user(s) (such as fall risk, depression risk, acuity score, demographic data, and the like), and the condition data 420 (which may or may not be present) generally corresponds to information relating to hospitalizations or facility admission of the user.

As discussed above, the user data 405 is used to generate one or more service plans 440, each with a corresponding outcome score 445. As discussed above, the service plans 440 can generally indicate a set of services to be provided to the user, and the outcome scores 445 generally indicate the expected success of the plan, such as the probability or likelihood that the user will be able to reside safely at home, the amount of time that is expected to elapse before any subsequent hospital or facility admission, and the like.

In the illustrated workflow 400, once a service plan 440 has been implemented (e.g., once it has been selected or approved by a clinician and admission or providing of the services begins), a monitoring system 450 can evaluate its efficacy in real-time (or near real-time). For example, the monitoring system 450 may periodically or continuous evaluate the user data 405 (e.g., the condition data 420) to determine whether the user has been admitted to any facilities. In at least one embodiment, while performing the service plan (e.g., providing therapy, making home modifications, and the like), clinicians or caregivers can note the user's progress or status, such as via natural language notes, or by selecting options (e.g., from a drop down or radio button in a GUI) indicating the status of the user. Although depicted as a discrete system for conceptual clarity, in embodiments, the monitoring system 450 may be implemented as a standalone service, or as part of the machine learning system 435 (or another system).

In the illustrated workflow, the monitoring system 450 generates feedback 455 based on the monitored service plan(s) 440. In one embodiment, the monitoring system 450 can receive explicit update from users (e.g., clinicians) indicating whether the service plan is working (e.g., whether the user is remaining safely at home). In some embodiments, the monitoring system 450 generates new feedback 445 each time the condition of a user changes. For example, if the user data 405 indicates that the user required admission to a hospital, the monitoring system 450 may generate feedback 455 indicating the corresponding service plan being used for the user, the portion(s) of the service plan that may be responsible for the failure, how long the plan had been in place prior to the admission, and the like.

In at least one embodiment, the monitoring system 450 may also generate feedback 455 indicating that a user condition has not changed. For example, if the user data 405 indicates that a given service plan has remained in place for a threshold period of time without the user being admitted or otherwise changing states or status (e.g., no admissions for a week, a month, and the like), the monitoring system 450 can generate feedback 455 indicating that the current service plan appears to be helping them remain safely at home.

In the illustrated workflow 400, the machine learning system 435 uses the feedback 455 to refine the machine learning model(s) used to generate and/or score service plans. For example, if the feedback 455 indicates that a specific user has remained safely at home, the machine learning system 435 may use the user's attributes, along with the current service plan for the user, as input to the model in order to generate a new outcome score 445 for the plan. The machine learning system 435 can then compare this generated score to the ground-truth (e.g., based on the newly-learned fact that the service plan is working), and use the resulting difference to refine the machine learning model(s). In this way, the machine learning system 435 can learn to generate better and more accurate service plans 440 and outcome scores 445 for future conditions.

In some embodiments, as discussed above, the machine learning system 435 may perform this model refinement whenever new feedback 455 is received. In other embodiments, the machine learning system 435 may defer the refinement until specified hours (e.g., overnight, or during non-peak times) to reduce the computational burden of the refinement. In one such embodiment, the machine learning system 435 (or another system) can store the feedback 455 to be periodically used during such defined times.

Figure 5:
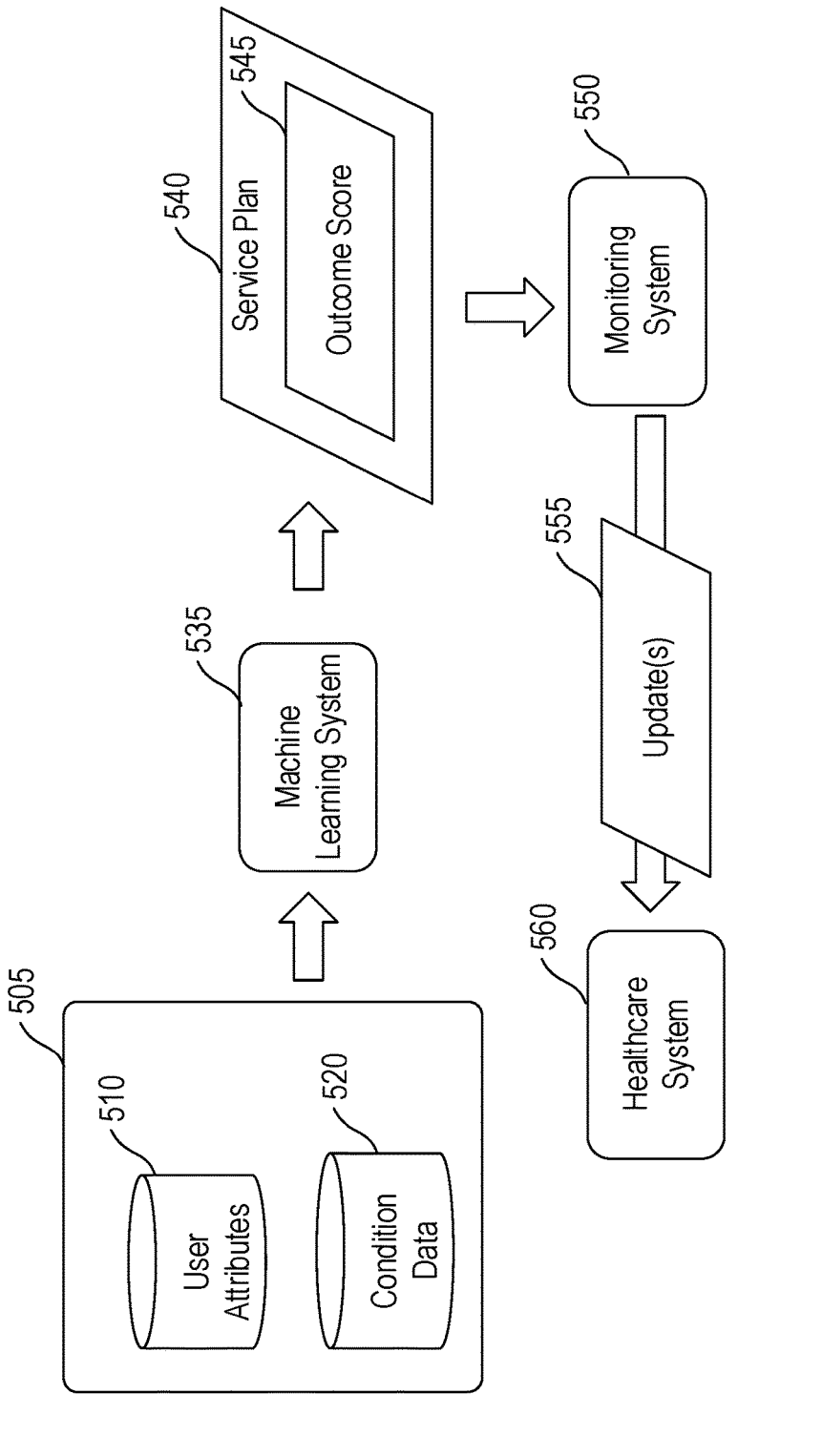
FIG. 5 depicts an example workflow for using machine learning models to generate service plans and automatically monitor plan efficacy.

Example Workflow for Using Machine Learning Models to Generate Service Plans and Automatically Monitor Plan Efficacy FIG. 5 depicts an example workflow 500 for using machine learning models to generate service plans and automatically monitor plan efficacy. In some embodiments, the workflow 500 is performed using trained models, such as the machine learning models 140 of FIG. 1.

The depicted workflow 500 differs from the workflow 400 of FIG. 4 in that it enables automatic plan monitoring and notification of interested third parties when relevant. In the illustrated workflow 500, a set of user data 505 is evaluated by a machine learning system 535 using one or more machine learning models (e.g., machine learning model 140 of FIG. 1) to generate and/or evaluate one or more service plan(s) 540, each with a corresponding outcome score 545. In embodiments, the machine learning system 535 may be implemented using hardware, software, or a combination of hardware and software. In some embodiments, the machine learning system 535 corresponds to the machine learning system 135 of FIG. 1, the machine learning system 235 of FIG. 2, the machine learning system 335 of FIG. 3, and/or the machine learning system 435 of FIG. 4. In other aspects, as discussed above, the machine learning system 535 may differ from the system that trained the model and/or generated the training data.

In some embodiments, the workflow 500 generally mirrors the workflow 400 of FIG. 4 to generate the service plans 540 and outcome scores 545. As discussed above, the user data 505 generally includes data or information associated with one or more users (also referred to as patients or residents). In the illustrated example, the user data 505 includes, for each user reflected in the data, a set of one or more user attributes 510 and/or condition data 520. As discussed above, the user attributes 510 generally include information relating to a set of one or more specified features, attributes, or characteristics describing the user(s) (such as fall risk, depression risk, acuity score, demographic data, and the like), and the condition data 520 (which may or may not be present) generally corresponds to information relating to hospitalizations or facility admission of the user.

As discussed above, the user data 505 is used to generate one or more service plans 540, each with a corresponding outcome score 545. As discussed above, the service plans 540 can generally indicate a set of services to be provided to the user, and the outcome scores 545 generally indicate the expected success of the plan, such as the probability or likelihood that the user will be able to reside safely at home, the amount of time that is expected to elapse before any subsequent hospital or facility admission, and the like.

In the illustrated workflow 500, once a service plan 540 has been implemented (e.g., once it has been selected or approved by a clinician and admission or providing of the services begins), a monitoring system 550 can evaluate its efficacy in real-time (or near real-time). For example, the monitoring system 550 may periodically or continuous evaluate the user data 505 (e.g., the condition data 520) to determine whether the user has been admitted to any facilities. In at least one embodiment, while performing the service plan (e.g., providing therapy, making home modifications, and the like), clinicians or caregivers can note the user's progress or status, such as via natural language notes, or by selecting options (e.g., from a drop down or radio button in a GUI) indicating the status of the user. Although depicted as a discrete system for conceptual clarity, in embodiments, the monitoring system 550 may be implemented as a standalone service, or as part of the machine learning system 535 (or another system).

In the illustrated workflow, the monitoring system 550 generates updates 555 based on the monitored service plan(s) 540. In one embodiment, the monitoring system 550 can receive explicit update from users (e.g., clinicians) indicating whether the service plan is working (e.g., whether the user is remaining safely at home). In some embodiments, the monitoring system 550 generates new updates 555 each time the condition of a user changes. For example, if the user data 505 indicates that the user required admission to a hospital, the monitoring system 550 may generate an update 555 indicating the corresponding service plan being used for the user, the portion(s) of the service plan that may be responsible for the failure, how long the plan had been in place prior to the admission, and the like.

In at least one embodiment, the monitoring system 550 may also generate updates 555 indicating that a user condition has not changed. For example, if the user data 505 indicates that a given service plan has remained in place for a threshold period of time without the user being admitted or otherwise changing states or status (e.g., no admissions for a week, a month, and the like), the monitoring system 550 can generate an update 555 indicating that the current service plan appears to be helping them remain safely at home.

In the illustrated workflow 500, the monitoring system 550 provides the update(s) 555 to one or more associated or interested entities or users, such as a healthcare system 560. That is, the monitoring system 550 may identify one or more users or other entities that are related to a given user or service plan, and transmit the update(s) 555 to these entities. For example, if the user was referred by another healthcare provider (e.g., a doctor that referred the user for in-home healthcare services), the monitoring system 550 may automatically provide the update 555 to the referring user (e.g., the doctor) to inform them as to how the service plan is proceeding.

Generally, the relevant or associated third parties may vary, but can include examples such as the referral source, the payer for the service plan (e.g., an insurer), a previous healthcare provider of the user, and the like.

In some aspects, the monitoring system 550 generates updates 555 for each specific user. In at least one aspect, the monitoring system 550 can additionally or alternatively generate collective or aggregate updates. For example, if a single entity (e.g., a hospital) is associated with multiple users, the monitoring system 550 may generate an update 555 that aggregates the information for each of the multiple users. Continuing this example, the update 555 may indicate the percentage of the users that required re-hospitalization or other admissions, the percentage that remain safely at home on their generated service plans, and the like.

Example Interface to Evaluate Service Plans

Figure 6:
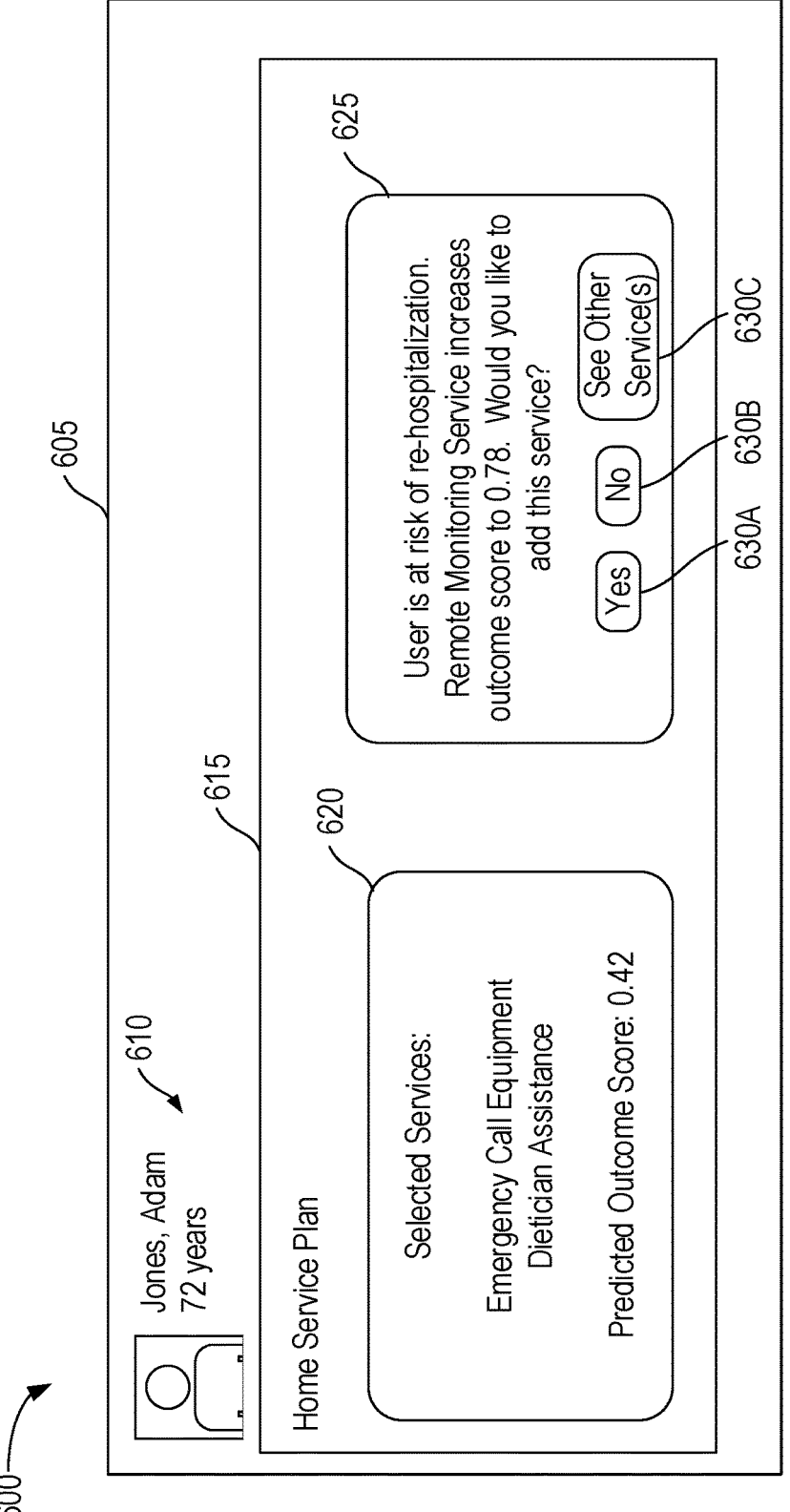
FIG. 6 depicts a graphical user interface for using machine learning to evaluate proposed service plans.

FIG. 6 depicts a graphical user interface (GUI) 600 for using machine learning to evaluate proposed service plans. In embodiments, users may access the GUI 600 using a variety of devices, including desktop computers, laptop computers, tablets, smartphones, access terminals in a healthcare facility, and the like.

The illustrated GUI 600 depicts a user profile 605 for a user needing one or more services in order to reside at home. In the illustrated example, the user profile 605 includes a first portion 610 for biographical data, including a picture of the user, the user's name, the user's age, and the like. In embodiments, other data (including more attributes not included in the illustrated example, as well as fewer attributes) may be displayed depending on the particular implementation.

In the illustrated example, the user profile 605 also includes a portion 615 that is used to provide home service planning for the user. Specifically, in the illustrated example, the portion 620 indicates the currently-selected and/or currently-used services for the user (e.g., selected by a clinician or other healthcare or service provider). In the illustrated example, the user currently utilizes emergency call equipment (e.g., a wearable device to rapidly request assistance, such as in the event of a fall) and dietician assistance (e.g., where a dietician assists with meal or recipe planning and/or preparation).

As illustrated, the portion 620 further includes a predicted outcome score. As discussed above, this score may indicate the probability or likelihood that the user will be able to remain at home (as opposed to requiring admission to a facility such as a hospital). In an embodiment, as discussed above, the predicted outcome score may be determined using one or more machine learning models. For example, a machine learning system (e.g., machine learning system 335 of FIG. 3) may process the user's attributes and the service plan to generate a score indicating the probability that the user will require hospitalization, the predicted length of time that will elapse before such admission, and the like.

In some embodiments, the projected outcome may be determined based further on the historical attributes of the particular user. For example, in addition to computing an outcome score using a model trained on a wide variety of data, the machine learning system may further evaluate the specific user's attributes to determine whether this specific service plan has already been attempted for the user, how much time the user has spent on the current plan, how many times (and how recently) the user has been hospitalized, and the like. In one such embodiment, if the user has already (unsuccessfully) used a given service plan, or if the user is currently on the service plan indications that they are worsening and may need more care, the machine learning system may reduce the outcome score to indicate that the specific service plan is less likely to succeed.

In the illustrated example, the predicted outcome score is 0.42. As indicated in block 625, the machine learning system has determined that the user is at risk of re-hospitalization if the indicated service plan is followed. For example, the machine learning system may determine that the predicted outcome score is below a defined threshold or otherwise fails to satisfy one or more criteria.

As illustrated, the machine learning system has further identified an alternative or modified service plan that would increase the outcome score (e.g., to 0.78), thereby reducing the probability that the user will require hospitalization. Specifically, in the illustrated example, the machine learning system has determined that adding a remote monitoring service to the user's home would provide improved security and safety. In some aspects, as discussed above, the machine learning system may evaluate the alternative sets of services using machine learning in order to identify which combination(s) result in the highest outcome score. The highest-scored alternative can then be output in the portion 625, if the selected plan meets certain criteria (e.g., a low predicted outcome score). In some aspects, if the ideal or optimal plan overlaps with the selected plan (e.g., where one or more services are included in both plans), the machine learning system can indicate the non-overlapping services (e.g., identifying the services that should be added, and/or identifying the services that should be removed, from the current plan).

In the illustrated example, the service provider may then use the buttons 630 to respond to the proposed modification. Specifically, the button 630A accepts the modification, the button 630B rejects it, and the button 630C prompts the system to display additional alternatives. In some aspects, upon selecting the button 630A, the system automatically implements the service plan (e.g., by ordering any needed equipment, contacting or engaging with third party providers, and the like).

In at least one aspect, if the provider selects the button 630B to reject the proposal, the system may optionally request feedback or reasoning as to why the proposal is being rejected. In some aspects, the machine learning system can use the rejection and/or feedback to further refine the model(s). For example, the machine learning system may infer or determine, based on the rejection and/or feedback, that a given service is inappropriate or not needed for users having similar attributes, that the suggested service is not needed or is inappropriate when combined with another service already included in the plan, and the like.

In some embodiments, if the user selects the button 630C, the machine learning system can output one or more alternative plans (e.g., the highest ranked plans), alongside an outcome score for each, and allow the user to select among them.

Example Interface to Generate Service Plans

Figure 7:
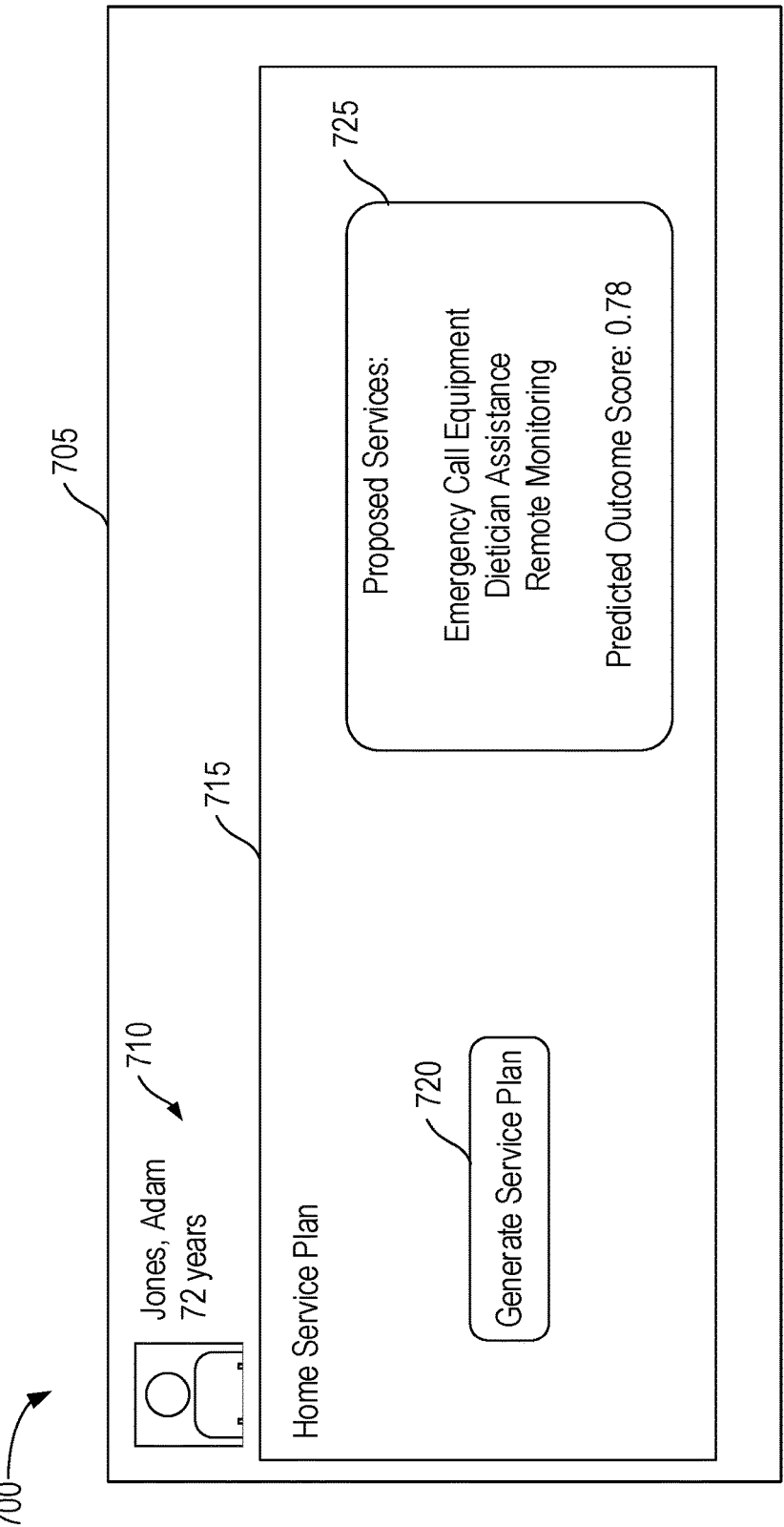
FIG. 7 depicts a graphical user interface for using machine learning to generate and optimize service plans.

FIG. 7 depicts a GUI 700 for using machine learning to generate and optimize service plans. In embodiments, users may access the GUI 700 using a variety of devices, including desktop computers, laptop computers, tablets, smartphones, access terminals in a healthcare facility, and the like.

The illustrated GUI 700 depicts a user profile 705 for a user needing one or more services in order to reside at home. The depicted GUI 700 may largely mirror the GUI 600 of FIG. 6, with the exception that the GUI 700 can be used to generate service plans in their entirety, rather than requiring that the provider manually define a proposed plan.

Specifically, in the illustrated example, the portion 715 corresponding to home service planning includes a button 720 that can be used to generate a service plan for the user. In an embodiment, when the button 720 is pressed, the machine learning system can generate a proposed service plan 725, and output the selected service(s) as well as the predicted outcome score.

In some aspects, as discussed above, to generate a service plan, the machine learning system can generate and evaluate a set of alternative plans (e.g., each possible combination of services) using one or more machine learning models. In some embodiments, the machine learning system generates the alternatives according to predefined criteria, such as rules indicating dependencies or requirements for one or more services. For example, a rule may indicate that a specific service is only applicable if the user has a specific attribute or set of attributes (e.g., an attribute indicating limited mobility and/or that the user has a two-story house may be required for an option such as installation of a chairlift to be applicable). As another example, a rule may indicate that two specific services are non-overlapping alternatives, in that the service plan cannot include both options (but may include neither). As another example, a rule may indicate that two specific services are required to be used together, in that if one of the services is selected, the other must also be used (though the plan may include neither).

By evaluating each possible alternative combination of services, the machine learning system can identify the service plan 725 having the highest score, and output this proposal to the provider. Though not included in the illustrated example, in some aspects, the GUI 700 may include one or more buttons or other inputs (such as the buttons 630 of FIG. 6), allowing the provider to accept, reject, and/or modify the proposed service plan. In some aspects, as discussed above, the machine learning system can use such input to refine the model(s) and generate better service plans for future requests.

Example Method for Training Machine Learning Models

FIG. 8 is a flow diagram depicting an example method 800 for training machine learning models to generate and evaluate service plans. In the illustrated embodiment, the method 800 is performed by a machine learning system, such as the machine learning system 135 of FIG. 1. In other embodiments, the method 800 can be performed by other systems, such as dedicated training systems.

Figure 9:
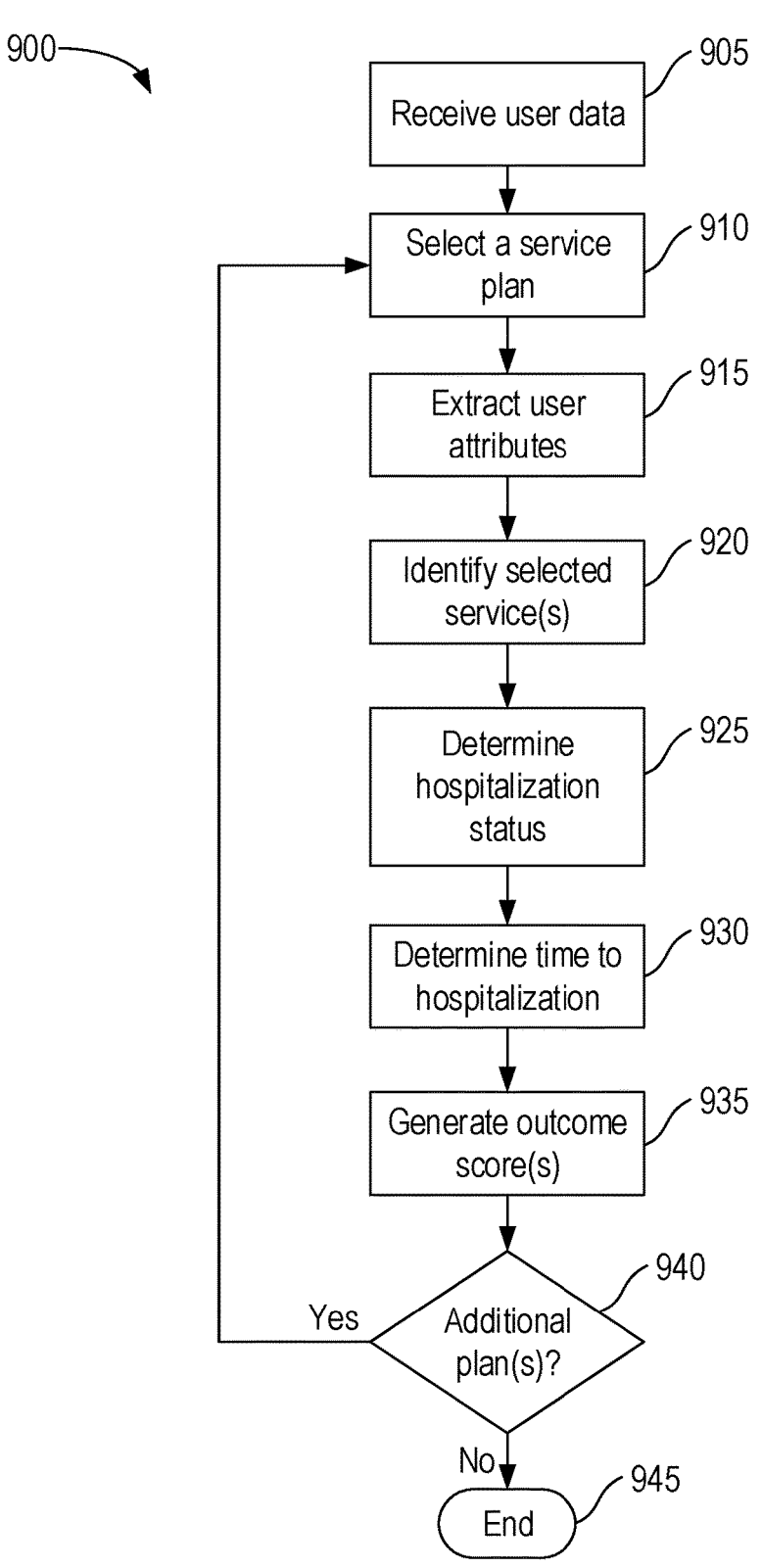
FIG. 9 is a flow diagram depicting an example method for generating training data for machine learning to evaluate service plans.

The method 800 begins at block 805, where the machine learning system receives training data (e.g., the training data generated using the workflow 200 of FIG. 2, and/or generated using the method 900 of FIG. 9). In embodiments, receiving the training data may include receiving it from one or more other systems (e.g., data aggregation or preprocessing systems), retrieving it from local or remote storage, and the like. In one embodiment, the training data can generally include multiple sets of user attributes, where each set of user attributes indicates the attributes or characteristics of a corresponding user during at a point or window of time associated with the selection or use of a corresponding service plan (e.g., within a defined window, such as one month prior, six months prior, and the like).

At block 810, the machine learning system selects one of the exemplars included in the training data. As used herein, an exemplar refers to a service plan (e.g., a defined set of services) and corresponding set of user attributes (e.g., corresponding to a defined or learned set of features) from a single user. For example, the attributes may correspond to those present during a defined point or window of time when the service plan was used or created. As an example, the exemplar may include indications as to the user fall risk, depression risk, and/or acuity score, the demographics of the user, whether the user had any specified diagnoses at the time, whether the user had been clinically assessed with one or more defined conditions during the window, medication(s) the user used or was prescribed or used during the window, and the like.

Generally, the exemplar may be selected using any suitable criteria (including randomly or pseudo-randomly), as the machine learning system will use all exemplars during the training process. Although the illustrated example depicts selecting exemplars sequentially for conceptual clarity, in embodiments, the machine learning system may select and/or process multiple exemplars in parallel.

At block 815, the machine learning system trains a machine learning model based on the selected exemplar. For example, the machine learning system may use the attributes and service plan indicated in the exemplar to generate an output outcome score or classification for the service plan, with respect to the user. As discussed above, this outcome score can generally indicate the predicted efficacy of the service plan, such as the probability that the service plan will allow the user to reside safely in their home, a predicted duration that will pass before the service plan fails (e.g., when hospitalization will be needed), and the like. In one such embodiment, lower values may indicate a lower probability that the user will be able to safely reside at home, while a higher value indicates that the user is relatively more likely to remain safe and stable.

During training, this score can then be compared against a ground-truth associated with the selected exemplar (e.g., an indication as to whether the user did, in fact, require subsequent admission). In some embodiments, this comparison includes determining how much time elapsed between the start of the service plan and any eventual admission. Based on this comparison, the parameters of the machine learning model can be updated. For example, if the generated outcome score is relatively low but the user did, in fact, avoid hospitalization (for at least some period of time), the machine learning system may modify the parameters such that the attributes and service plan in the exemplar result in a larger outcome score being generated.

At block 820, the machine learning system determines whether at least one additional exemplar remains in the training data. If so, the method 800 returns to block 810. If not, the method 800 continues to block 825. Although the illustrated example depicts iteratively refining the model using individual exemplars (e.g., using stochastic gradient descent), in some embodiments, the machine learning system can refine the model based on multiple exemplars simultaneously (e.g., using batch gradient descent).

At block 825, the machine learning system deploys the trained machine learning model for runtime use. In embodiments, this may include deploying the model locally (e.g., for runtime use by the machine learning system) and/or to one or more remote systems. For example, the machine learning system may distribute the trained model to one or more downstream systems (e.g., to one or more servers associated with specific care facilities, where these servers may use the model to evaluate service plans for users that are being discharged from or referred to specific facility).

Example Method for Generating Training Data for Machine Learning Models

FIG. 9 is a flow diagram depicting an example method 900 for generating training data for machine learning to evaluate service plans. In the illustrated embodiment, the method 900 is performed by a machine learning system, such as the machine learning system 235 of FIG. 2. In other embodiments, the method 900 can be performed by other systems, such as training systems, data generation and/or aggregation systems, and the like.

At block 905, the machine learning system receives user data (e.g., historical data 205 of FIG. 2). In an embodiment, the received user data can generally include data or information associated with one or more users (also referred to as patients or residents) from one or more prior points in time. That is, the treatment data may include, for one or more users, a set of service plan(s) used by the user at one or more points in time, where each service plan is associated with a set of characteristics or attributes of the user at the time. In some embodiments, the user data includes attributes for a set of users that receive in-home healthcare services.

In some embodiments, the received user data includes user data corresponding to a defined set of features to be used to generate a machine learning model to evaluate service plans, as discussed above. In some embodiments, the user data can include one or more indications, for each service plan reflected in the data, as to whether the service plan was successful (e.g., the user did not require hospitalization), the time that elapsed on the service plan until the plan no longer worked (e.g., until the user was hospitalized), and the like.

At block 910, the machine learning system selects one of the service plans reflected in the treatment data. Generally, this selection can be performed using any suitable technique (including randomly or pseudo-randomly), as all of the plans will be evaluated during the method 900. Although the illustrated example depicts an iterative or sequential selection and evaluation of each service plan, in some aspects, some or all of the method 900 may be performed in parallel. For example, rather than selecting and evaluating the data for each service plan individually, the machine learning system may process the data from some or all service plans sequentially or in parallel.

At block 915, the machine learning system extracts a set of user attributes associated with the selected service plan. For example, the machine learning system may extract relevant attributes corresponding to a defined window of time prior to the start of the service plan (e.g., in the month leading up to the selection of the plan). This can allow the machine learning system to generate a training data set that indicates sets of attributes that immediately-preceded selection of the service plan by a clinician or other provider. As discussed above, the attribute extraction may generally include extracting data relating to characteristics of the user that may impact the efficacy or success of the plan, such as fall risk, depression risk, the user's acuity score, demographics, diagnoses, clinical assessments, medications, and the like.

At block 920, the machine learning system identifies the combination of services that are included in the selected service plan. For example, as discussed above, the selected services may include various levels of home modifications, dietician assistance, in-home care, and the like.

At block 925, the machine learning system determines the hospitalization status (or other admission-related status, such as whether the user is admitted to a residential care facility) of the user with respect to the service plan. For example, the machine learning system may determine whether the user was hospitalized or otherwise admitted to a facility while the selected service plan was in place. In some aspects, if a hospitalization or admission occurred, the machine learning system can determine whether the admission was caused by a failure in the service plan, or by exogenous factors. For example, the machine learning system may determine whether the user was hospitalized due to a fall (which may indicate that the service plan was insufficient to ensure the user's safety and health), as opposed to due to some other illness (e.g., the flu) that is generally unrelated to the service plan.

At block 930, if the user was admitted to a hospital or other facility while using the selected service plan (and, in some aspects, if the admission was due to a fault or shortcoming in the plan), the machine learning system can determine how much time elapsed from when the plan was initiated until the admission. As discussed above, in some aspects, shorter durations may generally be correlated with lower outcome scores, while longer durations may be correlated with higher outcome scores. That is, a given service plan may have a relatively high score, even if hospitalization is predicted, if the predicted hospitalization is expected to occur substantially in the future (e.g., several years away).

At block 935, based on this data, the machine learning system can generate one or more outcome scores for the selected treatment plan. In one embodiment, the outcome score is generated or assigned by a healthcare provider. In some embodiments, the machine learning system uses an algorithmic or rules-based approach to define the outcome scores. In one embodiment, service plans that did not result in admission to a facility may be assigned higher scores, as compared to service plans that resulted in such admissions. Further, in some embodiments, the generated outcome score may be directly related to the time that passed until an admission (if one occurred) happened, such that shorter timelines result in lower scores, as compared to longer timelines.

In at least one embodiment, the outcome score is a binary value defined based on whether the user was subsequently admitted to a facility, whether any subsequent admission was beyond a defined duration from the initiation of the plan, and the like. These binary classifications can then be used as the target output of the model, allowing it to learn to generate continuous values (e.g., from zero to one) as outcome scores.

In some embodiments, as discussed above, the machine learning system may generate multiple outcome scores (or an outcome score having multiple components) for the service plan. For example, a first value or set of values may indicate whether the user was hospitalized, allowing a model to be trained to predict the efficacy of plans. A second value or set of values may indicate the time that elapsed until a subsequent admission, allowing a model to be trained to predict how much time will pass before the service plan becomes inadequate.

In this way, the machine learning system can build a training set that includes relevant attributes which affected the efficacy of various service plans. This data can be used to train one or more machine learning models, as discussed above and in more detail below, to predict the probability that a given service plan will work for a specific user, the time that will be needed, and the like.

At block 940, the machine learning system determines whether at least one additional service plan reflected in the user data has not been evaluated. If so, the method 900 returns to block 910. If not (e.g., if all service plans reflected in the user data have been evaluated), the method 900 terminates at block 945.

In some embodiments, the method 900 can be used periodically or upon other specified criteria (e.g., upon being triggered by a user or clinician) to generate or update training data used to train or refine one or more machine learning models. By iteratively using the method 900 (e.g., annually), the training data can be continuously or repeatedly updated, thereby allowing the machine learning system to refine the machine learning models to adjust to any changing conditions. This can significantly improve the accuracy and efficiency of such models.

Example Method for Identifying Eligible Users and Generating Service Plans

Figure 10:
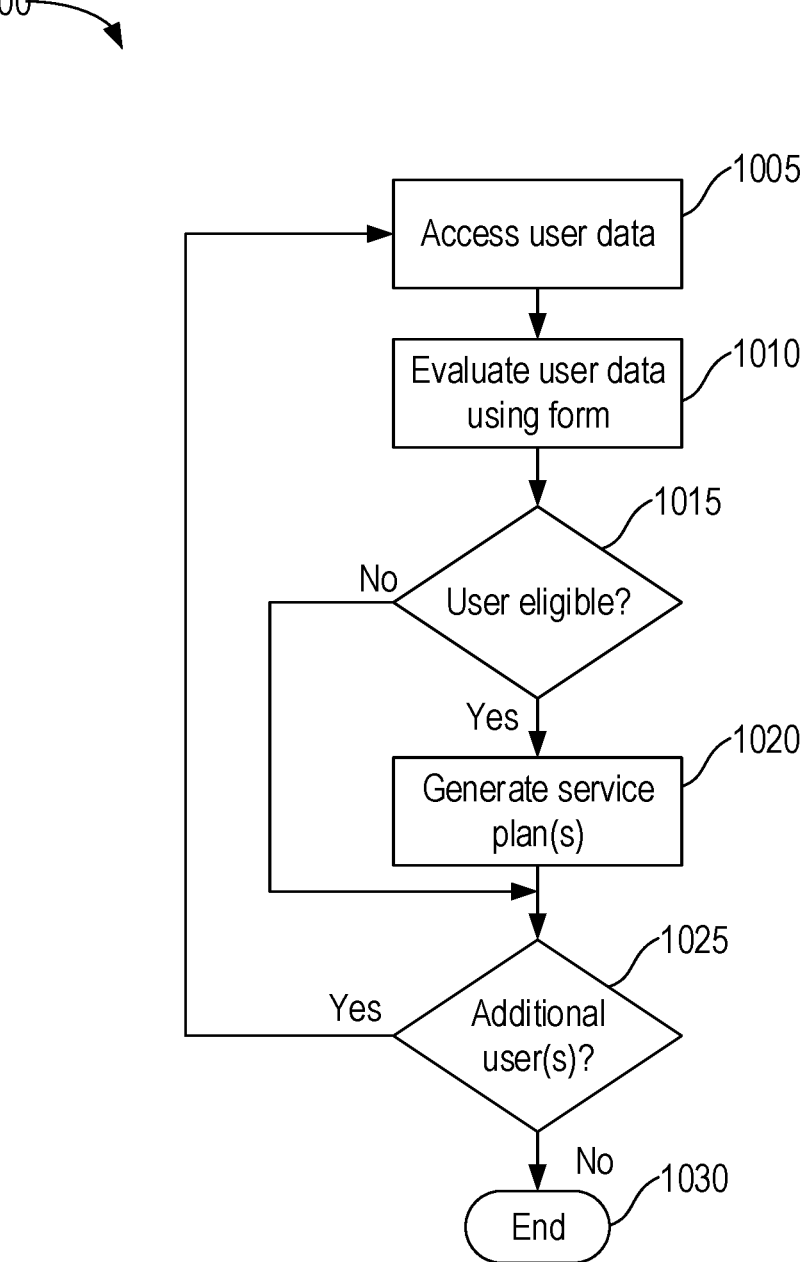
FIG. 10 is a flow diagram depicting an example method for identifying eligible users and generating service plans.

FIG. 10 is a flow diagram depicting an example method 1000 for identifying eligible users and generating service plans. In the illustrated embodiment, the method 1000 is performed by a machine learning system, such as the machine learning system 335 of FIG. 3, and/or the machine learning system 435 of FIG. 4, and/or the machine learning system 535 of FIG. 5. In other embodiments, the method 1000 can be performed by other systems, such as dedicated inferencing systems.

At block 1005, the machine learning system accesses user data for a user. For example, from a pool of potentially eligible users (e.g., users receiving care, who may benefit from receiving care at home), the machine learning system can select one of these users and access the selected user's data. In some aspects, the machine learning system can select the user using any suitable technique, including randomly or pseudo-randomly. In at least one embodiment, the machine learning system accesses the user's data in response to a care provider indicating the user (e.g., a physician indicating that they would like to determine whether the specific user is eligible for at-home care).

At block 1010, the machine learning system evaluates the user's data using a form (e.g., a set of rules, as discussed above). For example, as discussed above, the form may include a set of fields, each field indicating relevant user attributes (e.g., conditions or other characteristics). In some aspects, the machine learning system automatically populates the form based on the accessed user data. In some aspects, a user (e.g., the user receiving care and/or a care provider) inputs some or all of the data into the form.

As discussed above, the form can generally be used to determine or predict whether the user is eligible for or might benefit from in-home care. In some aspects, the form includes a set of rules, such as a rule indicating that a user is ineligible if they have certain conditions, is eligible if they have certain conditions, and the like. In some aspects, the form is used to generate a binary classification (e.g., eligible or not eligible) for the user. In some embodiments, the form can be used to generate a score (e.g., a value between one and five), where the score indicates the suitability of in-home care for the user (e.g., where the score may be directly or inversely proportional to the probability that in-home care is a good fit for the user).

At block 1015, the machine learning system determines whether the user is eligible, based on the form. For example, if the form outputs a binary classification, the machine learning system can determine whether the user is eligible by evaluating this classification. In some aspects, if the form returns a numerical score, the machine learning system can compare the score to one or more defined thresholds to determine whether the user is eligible (e.g., where only users with a score above or below a defined value are considered eligible).

If, at block 1015, the machine learning system determines that the user is not eligible, the method 1000 proceeds to block 1025, discussed in more detail below. If the machine learning system determines that the user is eligible, the method 1000 continues to block 1020.

At block 1020, the machine learning system generates one or more service plans for the user. In some embodiments, the service plan can be generated as discussed above. One example technique for generating the service plan for the user is discussed below in more detail with reference to FIG. 11. The method 1000 then continues to block 1025.

At block 1025, the machine learning system determines whether there is at least one additional user that has not been evaluated. If so, the method 1000 returns to block 1005. If not, the method 1000 terminates at block 1030.

Advantageously, by using the method 1000, the machine learning system can selectively use the machine learning model to generate and evaluate service plans only when the user is eligible for or otherwise may benefit from an in-home service plan. This can substantially reduce the computational expense of using the model, which thereby reduces the needed resources of the machine learning system and other computing systems.

Example Method for Using Machine Learning to
Evaluate Service Plan Alternatives

FIG. 11 is a flow diagram depicting an example method 1100 for generating and evaluating service plan alternatives using machine learning. In the illustrated embodiment, the method 1100 is performed by a machine learning system, such as the machine learning system 335 of FIG. 3, and/or the machine learning system 435 of FIG. 4, and/or the machine learning system 535 of FIG. 5. In other embodiments, the method 1100 can be performed by other systems, such as dedicated inferencing systems. In some embodiments, the method 1100 provides additional detail for block 1020 of FIG. 10.

At block 1105, the machine learning system selects a service plan alternative from a defined list of alternatives. For example, there may be a defined set of available services, and/or various characteristics or levels of each such service (e.g., part-time in-home assistance and full-time in-home assistance). These alternatives may be specified, for example, by one or more users (e.g., clinicians, doctors, service providers, and the like). In an embodiment, selecting a service plan alternative can include selecting one or more specific services (and, in some aspects, levels of service). In some aspects, the combinations of services are predefined. That is, the machine learning system may select from among a set of defined combinations of services. In at least one aspect, the machine learning system can select services to generate a combination of services, and use this combination as the service plan alternative.

In at least one aspect, as discussed above, the machine learning system can generate the service plan based on defined criteria or requirements, such as rules specifying when particular services may be useful, rules specifying when particular services cannot be used (or must be used), and the like. For example, if nutrition is adequate and/or insulin levels are stable for a diabetic patient, a service such as dietician service may be not needed and therefore not suggested as part of an alternative service plan. In some embodiments, in generating the service plan alternatives, the machine learning system can consider features such as cost and/or reimbursement options (e.g., based on insurance).

Generally, selecting/generating the service plan alternative at block 1100 can be performed using any technique (including randomly or pseudo-randomly), as the machine learning system may evaluate each alternative or combination during the method 1100. Although an iterative or sequential process is depicted for conceptual clarity, in some embodiments, the machine learning system may evaluate some or all of the service plans in parallel.

At block 1110, the machine learning system generates a predicted outcome score for the selected service plan alternative (e.g., for the combination of services). For example, as discussed above, the machine learning system may process the service plan (e.g., indications of the included services), along with the user's attributes (such as their age, diagnoses, fall risk, depression risk, acuity score, demographic data, and the like), as input to a machine learning model trained to predict whether the user will require future hospitalization or admission to another facility if the in-home healthcare service plan is followed. In some embodiments, as discussed above, this may include use of one or more models, and may include generating predictions relating to whether hospitalization will occur, how much time will elapse before hospitalization occurs, and the like.

At block 1115, the machine learning system determines whether there is at least one additional service plan alternative that has not-yet been evaluated. If so, the method 1100 returns to block 1105. If not, the method 1100 continues to block 1120. Advantageously, the machine learning system can thereby enable a wide variety of service plans (including every possible combination of component services, in some embodiments) to be considered for the user. As there may be a large number of such combinations (e.g., thousands), the machine learning system can therefore enable caregivers to provide highly-tailored plans for the specific user (which the caregiver could not otherwise do manually or mentally).

At block 1120, the machine learning system ranks the service plan alternatives based on the generated outcome scores. In some embodiments, the machine learning system can additionally or alternatively filter the service plan alternatives. For example, a user may indicate that they want to filter out any service plans with an outcome score below a defined threshold, with a timeline less than a target date, and the like.

At block 1125, the machine learning system then outputs one or more of the highest-ranked service plan alternatives, such as via the GUIs 600 and/or 700 of FIGS. 6 and 7. In this way, the user is able to rapidly review the alternative service plan options, selecting the plan that is most likely to result in beneficial results for the user.

Figure 12:
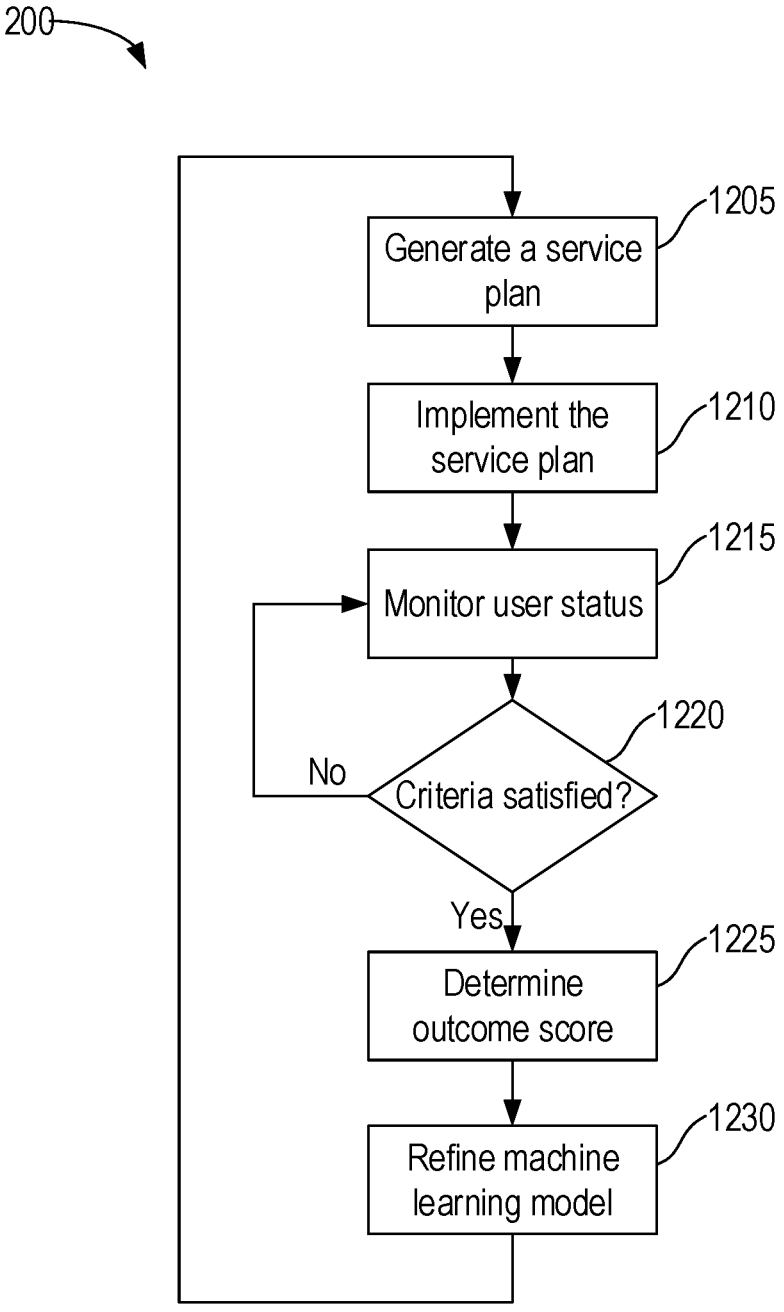
FIG. 12 is a flow diagram depicting an example method for refining machine learning models to generate and evaluate service plans.

Example Method for Refining Machine Learning
Models to Generate and Evaluate Service Plans FIG. 12 is a flow diagram depicting an example method 1200 for refining machine learning models to generate and evaluate service plans. In the illustrated embodiment, the method 1200 is performed by a machine learning system, such as the machine learning system 435 of FIG. 4. In other embodiments, the method 1200 can be performed by other systems, such as dedicated training or refinement systems.

At block 1205, the machine learning system can generate one or more service plans for a user during runtime. That is, the machine learning system may deploy and use a trained machine learning model to process user data in order to generate outcome scores for one or more service plans at runtime, and select one or more of these plans for use. For example, the machine learning system may automatically use the model(s) to generate outcome scores for all possible service plans for a user. Similarly, the machine learning system may automatically generate new scores whenever new data becomes available. In some embodiments, a clinician can selectively use the machine learning system to generate outcome scores and service plans as needed.

At block 1210, the machine learning system implements the service plan. In some embodiments, implementing the service plan can include outputting it to a user (e.g., a clinician) for review and approval. In some aspects, implementing the service plan can include automatically enacting one or more of the underlying services, such as ordering equipment (e.g., chairlifts), engaging or requesting services (e.g., hiring a dietician), and the like. Once the service plan is in place, the user begins receiving care and assistance according to the plan. One example technique for implementing the service plan is discussed in more detail below with reference to FIG. 14.

At block 1215, the machine learning system (or another system, such as the monitoring system 450 of FIG. 4) monitors the user condition(s) to determine whether any changes occur (such as whether they are admitted to a hospital or other facility, or whether their state is declining).

At block 1220, the machine learning system determines whether one or more defined criteria are satisfied. In some embodiments, the criteria can include an indication that the user condition as changed (such as determined based on the monitoring of block 1215 above). In some embodiments, the criteria may include explicit feedback from a clinician (e.g., indicating that the service plan is inadequate or inappropriate, indicating that the user is no longer following the service plan for other reasons, and the like). In at least one embodiment, the criteria can include determining whether a defined period of time has elapsed.

If, at block 1220, the machine learning system determines that none of the criteria have passed, the method 1200 returns to block 1215. If at least one of the criteria is satisfied, the method 1200 continues to block 1225, where the machine learning system determines an outcome score for the service plan based on the user's current condition. In one embodiment, the machine learning system determines the outcome score by evaluating the user attributes to determine whether the user was hospitalized. Generally, determining that the user has not been admitted to a healthcare facility will result in a higher outcome score, as compared to a determination that the user has been so admitted. In some embodiments, the outcome score is determined based in part on the length of time that has elapsed since the service plan was begun (e.g., where shorter times may be inversely related to the score).

Once the outcome score for the relevant service plan has been generated, the method 1200 continues to block 1230. At block 1230, the machine learning system refines the trained machine learning model(s) based on this updated outcome score. For example, if the generated outcome score for a user was relatively low, but the new data indicates that the user has not needed hospitalization or other admission, the machine learning system may use the prior set of attributes (used to generate the original score) as exemplar input that should be correlated with a high outcome score (alongside the selected service plan). Similarly, if the generated outcome score was relatively high but the new data indicates the user was hospitalized, the machine learning system may refine the model to indicate that such attributes should be correlated to a lower score.

The method 1200 then returns to block 1205. In this way, the machine learning system can continuously or periodically refine the machine learning model(s), thereby ensuring that they continue to produce highly-accurate score predictions for users.

Example Method for Using Machine Learning to Track Service Plan Efficacy

Figure 13:
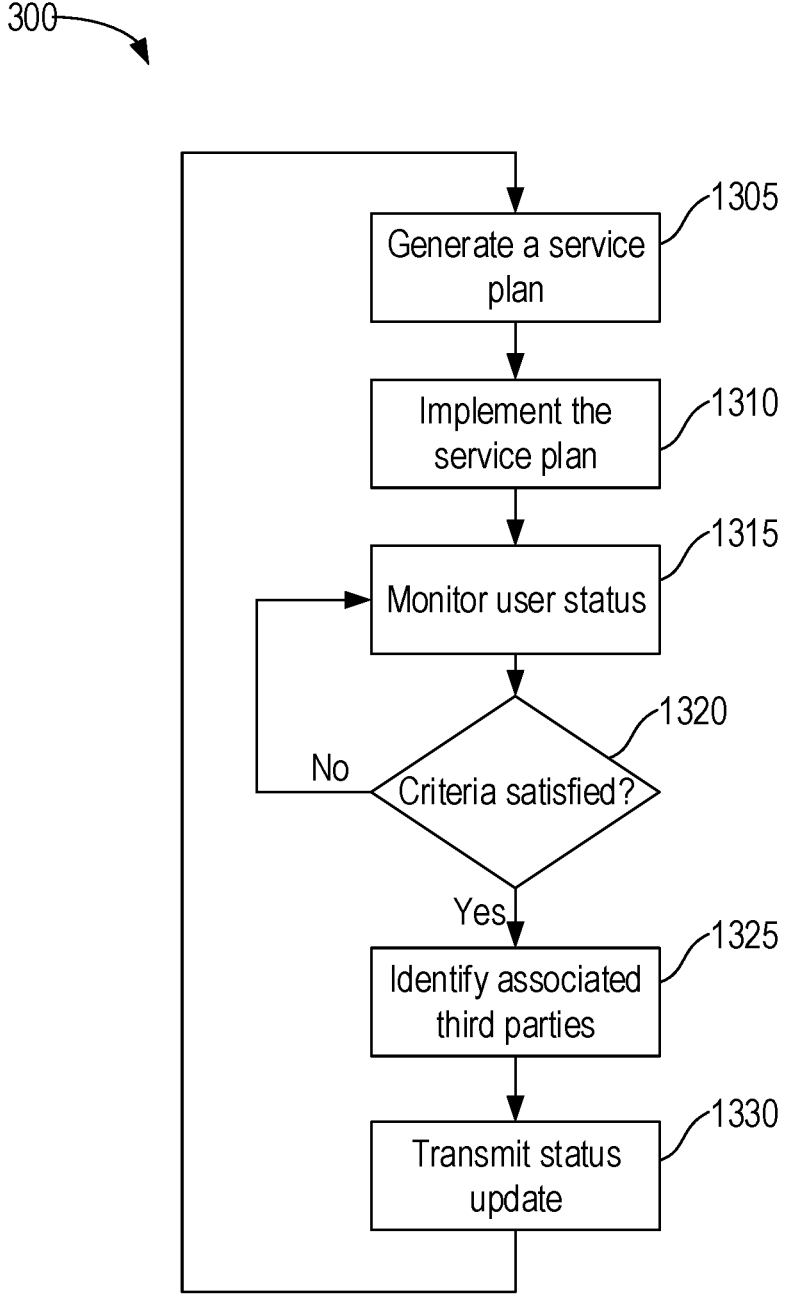
FIG. 13 is a flow diagram depicting an example method for using machine learning models to generate service plans and automatically monitor plan efficacy.

FIG. 13 is a flow diagram depicting an example method 1300 for using machine learning models to generate service plans and automatically track service plan efficacy. In the illustrated embodiment, the method 1300 is performed by a machine learning system, such as the machine learning system 535 of FIG. 5. In other embodiments, the method 1300 can be performed by other systems.

In some aspects, portions of the method 1300 may partially or entirely overlap with portions of the method 1200 of FIG. 12. For example, blocks 1305, 1310, 1315, and 1325 may mirror the operations of blocks 1205, 120, 1215, and 1225, respectively, in FIG. 12.

At block 1305, the machine learning system can generate one or more service plans for a user during runtime, as discussed above. That is, the machine learning system may deploy and use a trained machine learning model to process user data in order to generate outcome scores for one or more service plans at runtime, and select one or more of these plans for use.

At block 1310, the machine learning system implements the generated service plan. In some embodiments, implementing the service plan can include outputting it to a user (e.g., a clinician) for review and approval, and/or automatically enacting one or more of the underlying services. One example technique for implementing the service plan is discussed in more detail below with reference to FIG. 14.

At block 1315, the machine learning system (or another system, such as the monitoring system 550 of FIG. 5) monitors the user condition(s) to determine whether any changes occur (such as whether they are admitted to a hospital or other facility, or whether their state is declining).

At block 1320, the machine learning system determines whether one or more defined criteria are satisfied. In some embodiments, the criteria can include an indication that the user condition as changed (such as determined based on the monitoring of block 1315 above).

If, at block 1320, the machine learning system determines that none of the criteria have been satisfied, the method 1300 returns to block 1315. If at least one of the criteria is satisfied, the method 1300 continues to block 1325, where the machine learning system identifies one or more associated third parties for the user and/or service plan. For example, as discussed above, the machine learning system may identify the doctor or other entity that referred the user to the service provider, the entity that pays for all or a portion of the services received by the user, an entity specifically identified by the user (e.g., a relative, friend, guardian, or individual with a healthcare power of attorney for the user), and the like.

At block 1330, the machine learning system transmits a status update to the identified third party or parties. For example, in the case of a referral source that referred the user to the service provider, the update may include information such as the user's identity, the date of the referral, the service(s) that were provided, and the current state or status of the user (e.g., whether they are or have been hospitalized). This allows the machine learning system to automatically keep relevant parties updated when new information becomes available.

In some aspects, as discussed above, the machine learning system can additionally or alternatively generate aggregated updates based on data from a number of users. For example, if a given entity (e.g., a hospital) is associated with multiple users (e.g., acting as the referral source), the machine learning system may periodically generate an aggregate update on these users (e.g., indicating the various services being provided, indicating the number or percentage of them that still reside at home, indicating the number or percentage that have required hospitalization or other healthcare facility admission, and the like).

The method 1300 then returns to block 1305. In this way, the machine learning system can continuously or periodically monitor the users, thereby ensuring that affected or relevant third parties remain informed as to how well the system is working.

Example Method for Automatically Implementing Service Plans

FIG. 14 is a flow diagram depicting an example method 1400 for automatically implementing service plans. In the illustrated embodiment, the method 1400 is performed by a machine learning system, such as the machine learning system 335 of FIG. 3, the machine learning system 435 of FIG. 4, and/or the machine learning system 535 of FIG. 5. In other embodiments, the method 1400 can be performed by other systems. In one embodiment, the method 1400 provides additional detail for block 1210 of FIG. 12 and/or block 1310 of FIG. 13.

In some aspects, the method 1400 is performed after a service plan is selected and/or approved by a care provider. In at least one aspect, the method 1400 is automatically instantiated as soon as a service plan is activated or otherwise accepted.

At block 1405, the machine learning system identifies the calendar of the user for whom the service plan is being implemented. For example, the machine learning system may identify any prior engagements the user has scheduled for one or more days or times in the future, if such engagements might interfere with activating or implementing the service plan. For example, if one aspect of the service plan is a weekly visit from a physician, the machine learning system may evaluate the user's calendar to determine whether there are any times or dates when such a visit is not possible (e.g., due to a scheduled event such as a weekly book club that the user attends.

At block 1410, the machine learning system selects a service from the service plan that is being implemented. In some aspects, the machine learning system selects the service randomly or pseudo-randomly. In at least one aspect, the machine learning system selects the service based on priority or importance of each service. For example, some services may have a higher priority (such as a visit from a physician) as compared to other services with lower priority (such as a visit from a dietician). In some aspects, in selecting the service, the machine learning system can additionally or alternatively consider whether any services have a deadline when they must be completed. For example, if home modifications are needed (e.g., to repair a broken handrail or stairway), the machine learning system may determine that this service has the highest priority, as it must be complete before the user returns to their home. By selecting high-priority services first, the machine learning system can ensure that these items are complete as soon as possible.

At block 1415, the machine learning system identifies potential servicers for the selected service. For example, the machine learning system may identify a set of service providers that are capable of performing the service (e.g., that have characteristics or attributes matching the service), and determine the availability of each to perform the service (e.g., by querying the servicer for their schedule, accessing an application programming interface (API) provided by the servicer, and the like).

At block 1420, the machine learning system then schedules the selected service based on the potential servicer's availabilities and the user's calendar. In some aspects, the machine learning system schedules the earliest-available servicer to provide the service. That is, the machine learning system can find the earliest service appointment that fits the user's calendar, and schedule this service at this time.

In at least one aspect, the machine learning system schedules services so as to avoid having multiple services being provided on the same day. For example, if the user needs a physician visit, dietician visit, and nurse practitioner visit, the machine learning system can ensure that each of these service providers visits on a separate day (rather than all on the same day). This can reduce fatigue to the user, as well as expanding oversight and care (e.g., because a new care provider interacts with the service each day), providing additional interactions on different days. This can reduce or prevent decline, or enable care providers to rapidly identify such declines.

At block 1425, the machine learning system determines whether there is at least one additional service that is yet-to-be scheduled. If so, the method 1400 returns to block 1410. If not, the method 1400 terminates at block 1430.

Example Method for Training Machine Learning Models to Evaluate Service Plans FIG. 15 is a flow diagram depicting an example method 300 for training machine learning models to improve service planning. In the illustrated embodiment, the method 1500 is performed by a machine learning system, such as the machine learning system 135 of FIG. 1. In other embodiments, the method 1500 can be performed by other systems, such as dedicated training systems.

At block 1505, service data (e.g., historical data 105 of FIG. 1) describing a healthcare service plan for a user is received, wherein the healthcare service plan comprises a set of one or more home healthcare services provided to the user At block 1510, an outcome score (e.g., outcome score 245 of FIG. 2) is generated by processing the service data, wherein the outcome score is based at least in part on whether the user was hospitalized while on the healthcare service plan.

At block 1515, a machine learning model (e.g., machine learning model 140 of FIG. 1) is trained to generate healthcare service plans based on the outcome score.

At block 1520, the trained machine learning model is deployed.

Example Method for Generating Service Plans Using Machine Learning

FIG. 16 is a flow diagram depicting an example method 1600 for generating and evaluating service plans using trained machine learning models. In the illustrated embodiment, the method 1600 is performed by a machine learning system, such as the machine learning system 335 of FIG. 3. In other embodiments, the method 1600 can be performed by other systems, such as dedicated inferencing systems.

At block 1605, user data (e.g., user data 305 of FIG. 3) describing one or more conditions of a user is received.

At block 1610, a first plurality of user attributes (e.g., user attributes 310 of FIG. 3) is extracted, from the user data, for the user.

At block 1615, a first alternative healthcare service plan (e.g., service plan 340 of FIG. 3) having a set of one or more home healthcare services to be provided to the user is selected.

At block 1620, a first predicted outcome score (e.g., outcome score 345 of FIG. 3) is generated by inputting the first alternative healthcare service plan and the first plurality of user attributes into a trained machine learning model.

At block 1625, the first healthcare service plan is implemented for the user based at least in part on the first predicted outcome score.

Example Processing System for Improved Machine Learning

Figure 17:
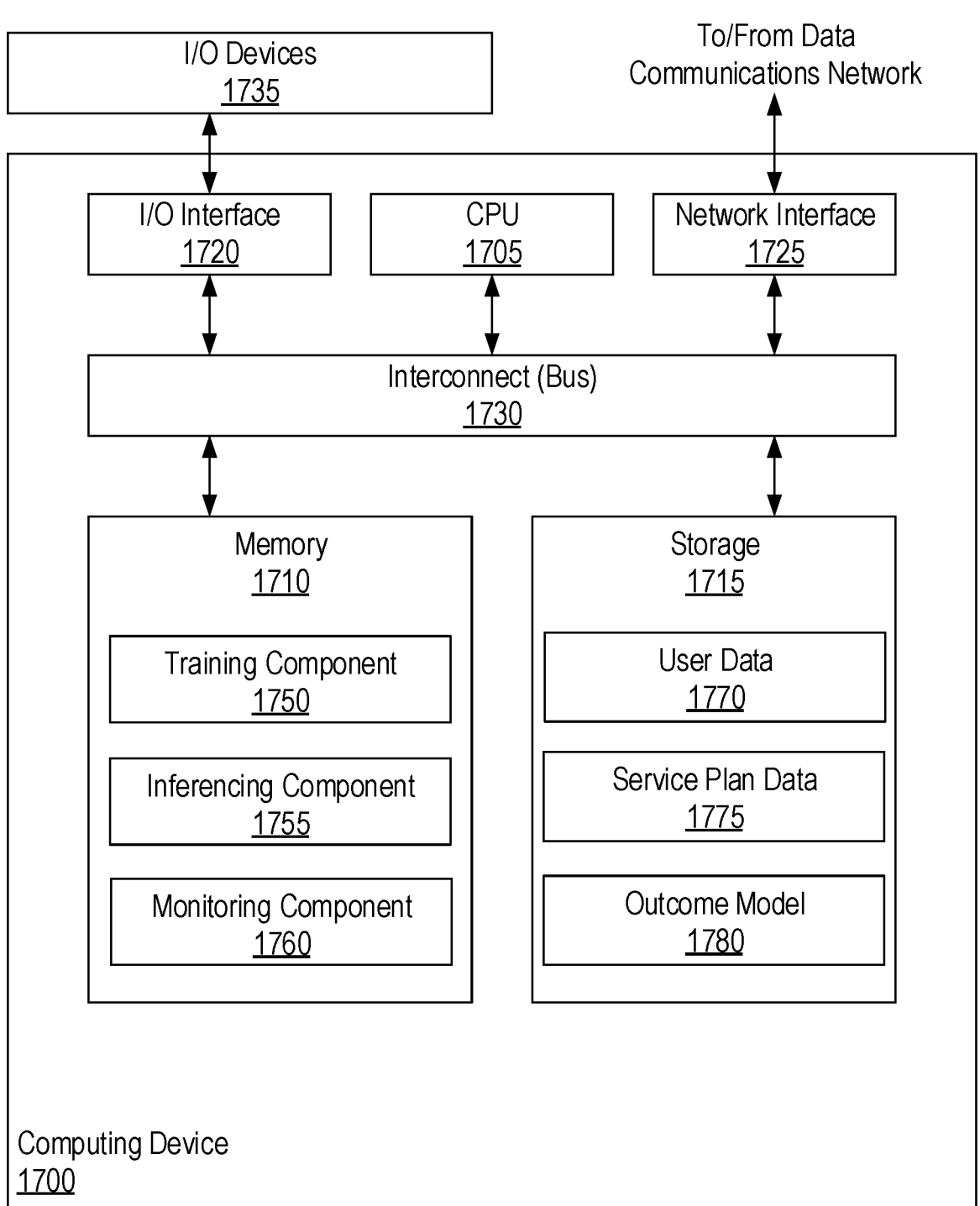
FIG. 17 depicts an example computing device configured to perform various aspects of the present disclosure.

FIG. 17 depicts an example computing device 1700 configured to perform various aspects of the present disclosure. Although depicted as a physical device, in embodiments, the computing device 1700 may be implemented using virtual device(s), and/or across a number of devices (e.g., in a cloud environment). In one embodiment, the computing device 1700 corresponds to the machine learning system 135 of FIG. 1, the machine learning system 235 of FIG. 2, the machine learning system 335 of FIG. 3, the machine learning system 435 of FIG. 4, and/or the machine learning system 535 of FIG. 5.

As illustrated, the computing device 1700 includes a CPU 1705, memory 1710, storage 1715, a network interface 1725, and one or more I/O interfaces 1720. In the illustrated embodiment, the CPU 1705 retrieves and executes programming instructions stored in memory 1710, as well as stores and retrieves application data residing in storage 1715. The CPU 1705 is generally representative of a single CPU and/or GPU, multiple CPUs and/or GPUs, a single CPU and/or GPU having multiple processing cores, and the like. The memory 1710 is generally included to be representative of a random access memory. Storage 1715 may be any combination of disk drives, flash-based storage devices, and the like, and may include fixed and/or removable storage devices, such as fixed disk drives, removable memory cards, caches, optical storage, network attached storage (NAS), or storage area networks (SAN).

In some embodiments, I/O devices 1735 (such as keyboards, monitors, etc.) are connected via the I/O interface(s) 1720. Further, via the network interface 1725, the computing device 1700 can be communicatively coupled with one or more other devices and components (e.g., via a network, which may include the Internet, local network(s), and the like). As illustrated, the CPU 1705, memory 1710, storage 1715, network interface(s) 1725, and I/O interface(s) 1720 are communicatively coupled by one or more buses 1730.

In the illustrated embodiment, the memory 1710 includes a training component 1750, an inferencing component 1755, and a monitoring component 1760, which may perform one or more embodiments discussed above. Although depicted as discrete components for conceptual clarity, in embodiments, the operations of the depicted components (and others not illustrated) may be combined or distributed across any number of components. Further, although depicted as software residing in memory 1710, in embodiments, the operations of the depicted components (and others not illustrated) may be implemented using hardware, software, or a combination of hardware and software.

In one embodiment, the training component 1750 is used to generate training data and/or to train machine learning models (e.g., based on historical training data), as discussed above. The inferencing component 1755 may generally be used to identify eligible users, generate outcome scores and/or generate or select service plans for users, and/or implement service plans for users, as discussed above. The monitoring component 1760 may be configured to monitor user status updates in order to refine the model(s) and/or inform relevant third parties, as discussed above.

In the illustrated example, the storage 1715 includes user data 1770 (which may correspond to historical data, such as historical data 105 of FIG. 1, historical data 205 of FIG. 2, user data 305 of FIG. 3, user data 405 of FIG. 4, and/or user data 505 of FIG. 5), as well as service plan data 1775 (which may indicate the available service alternatives, and/or include information relating to the services that were previously used and/or are currently used for one or more users). The storage 1715 also includes an outcome model 1780 (which may correspond to the machine learning model 140 of FIG. 1). Although depicted as residing in storage 1715, the user data 1770, service plan data 1775, and outcome model 1780 may be stored in any suitable location, including memory 1710.

EXAMPLE CLAUSES

Implementation examples are described in the following numbered clauses:

Clause 1: A method, comprising: receiving service data describing a healthcare service plan for a user, wherein the healthcare service plan comprises a set of one or more home healthcare services provided to the user; generating an outcome score by processing the service data, wherein the outcome score is based at least in part on whether the user was hospitalized while on the healthcare service plan; training a machine learning model to generate healthcare service plans based on the outcome score; and deploying the trained machine learning model.

Clause 2: The method of Clause 1, wherein the healthcare service plan comprises at least one of: one or more home modifications, remote monitoring, emergency call equipment, dietician assistance, one or more therapies, or in-home assistance from a healthcare provider.

Clause 3: The method of any one of Clauses 1-2, wherein generating the outcome score comprises: determining, based on the service data, that the user was hospitalized while on the healthcare service plan; determining, based on the service data, an amount of time that elapsed between a start of the healthcare service plan and a time when the user was hospitalized; and computing the outcome score based at least in part on the amount of time.

Clause 4: The method of any one of Clauses 1-3, further comprising: extracting, from the service data, a plurality of user attributes describing the user; and training the machine learning model based further on the plurality of user attributes.

Clause 5: The method of any one of Clauses 1-4, wherein training the machine learning model comprises: generating a predicted outcome score by processing the healthcare service plan and the plurality of user attributes using the machine learning model; and refining the machine learning model based on a difference between the predicted outcome score and the outcome score.

Clause 6: A method, comprising: receiving user data describing one or more conditions of a user; generating a first healthcare service plan for the user, comprising: extracting a first plurality of user attributes, from the user data, for the user; selecting a first alternative healthcare service plan having a set of one or more home healthcare services to be provided to the user; and generating a first predicted outcome score by inputting the first alternative healthcare service plan and the first plurality of user attributes into a trained machine learning model; and implementing the first healthcare service plan for the user based at least in part on the first predicted outcome score.

Clause 7: The method of Clause 6, wherein implementing the first healthcare service plan comprises: outputting the first healthcare service plan to a healthcare provider; receiving approval, from the healthcare provider, of the first healthcare service plan; determining a calendar of the user; and for each respective home healthcare service in the first healthcare service plan: identifying a respective servicer to provide the respective home healthcare service; and scheduling the respective servicer to provide the respective home healthcare service based on the calendar of the user.

Clause 8: The method of any one of Clauses 6-7, wherein outputting the first healthcare service plan comprises displaying the set of one or more home healthcare services and the first predicted outcome score on a graphical user interface (GUI).

Clause 9: The method of any one of Clauses 6-8, wherein generating the first healthcare service plan comprises: generating a plurality of predicted outcome scores by processing a plurality of alternate healthcare service plans using the trained machine learning model; and selecting the first healthcare service plan based on determining that the first predicted outcome score is greater than each of the plurality of predicted outcome scores.

Clause 10: The method of any one of Clauses 6-9, wherein the first healthcare service plan comprises at least one of: one or more home modifications, remote monitoring, emergency call equipment, dietician assistance, one or more therapies, or in-home assistance from a healthcare provider.

Clause 11: The method of any one of Clauses 6-10, wherein the first healthcare service plan enables the user to reside at home with reduced risk of harm or hospitalization, as compared to at least a second healthcare service plan having a different set of one or more home healthcare services.

Clause 12: The method of any one of Clauses 6-11, further comprising: determining whether the user was hospitalized while on the first healthcare service plan; and refining the trained machine learning model based on whether the user was hospitalized.

Clause 13: The method of any one of Clauses 6-12, further comprising: identifying a third party associated with the user, wherein the third party comprises at least one of: a referral source of the user, a payer for the first healthcare service plan, or a previous healthcare provider of the user; and automatically transmitting, to the third party, an indication of whether the user was hospitalized while on the first healthcare service plan.

Clause 14: The method of any one of Clauses 6-13, further comprising, upon determining that at least one of the first plurality of user attributes changed after the first healthcare service plan was implemented: extracting a new plurality of user attributes for the user; selecting a new healthcare service plan; and generating a new predicted outcome score by processing the new healthcare service plan and the new plurality of user attributes using the trained machine learning model.

Clause 15: A system, comprising: a memory comprising computer-executable instructions; and one or more processors configured to execute the computer-executable instructions and cause the processing system to perform a method in accordance with any one of Clauses 1-14.

Clause 16: A system, comprising means for performing a method in accordance with any one of Clauses 1-14.

Clause 17: A non-transitory computer-readable medium comprising computer-executable instructions that, when executed by one or more processors of a processing system, cause the processing system to perform a method in accordance with any one of Clauses 1-14.

Clause 18: A computer program product embodied on a computer-readable storage medium comprising code for performing a method in accordance with any one of Clauses 1-14.

ADDITIONAL CONSIDERATIONS

The preceding description is provided to enable any person skilled in the art to practice the various embodiments described herein. The examples discussed herein are not limiting of the scope, applicability, or embodiments set forth in the claims. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, the word "exemplary" means "serving as an example, instance, or illustration." Any aspect described herein as "exemplary" is not necessarily to be construed as preferred or advantageous over other aspects.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications or systems (e.g., the machine learning system 135) or related data available in the cloud. For example, the machine learning system could execute on a computing system in the cloud and train and/or use machine learning models. In such a case, the machine learning system 135 could train models to evaluate service plans, and store the models at a storage location in the cloud. Doing so allows a user to access this information from any computing system attached to a network connected to the cloud (e.g., the Internet).

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A method, comprising:

receiving service data describing a healthcare service plan for a user, wherein the healthcare service plan comprises a set of home healthcare services provided to the user, in a residence of the user, during a first window of time;

generating an outcome score by processing the service data, wherein the outcome score is based at least in part on whether the user was hospitalized while on the healthcare service plan during a second window of time subsequent to the first window of time, comprising:

determining, based on the service data, that the user was hospitalized while on the healthcare service plan;

determining, based on the service data, an amount of time that elapsed between a start of the healthcare service plan and a time when the user was hospitalized; and computing the outcome score based at least in part on the amount of time;

training a machine learning model to evaluate healthcare service plans based on the outcome score, comprising:

processing the set of home healthcare services using the machine learning model to generate a predicted outcome of the healthcare service plan if the set of home healthcare services are provided to the user in the residence of the user; and updating one or more parameters of the machine learning model based on a difference between the predicted outcome and the outcome score; and deploying the trained machine learning model;

generating a first predicted outcome score by processing a first healthcare service plan using the trained machine learning model;

generating a plurality of predicted outcome scores by processing a plurality of alternate healthcare service plans using the trained machine learning model; and selecting a first healthcare service plan based on determining that the first predicted outcome score is greater than each of the plurality of predicted outcome scores.

2. The method of claim 1, wherein the healthcare service plan comprises at least one of:

one or more home modifications, remote monitoring, emergency call equipment, dietician assistance, one or more therapies, or in-home assistance from a healthcare provider.

3. The method of claim 1, further comprising:

extracting, from the service data, a plurality of user attributes describing the user; and training the machine learning model based further on the plurality of user attributes.

4. The method of claim 3, wherein training the machine learning model comprises:

generating a predicted outcome score by processing the healthcare service plan and the plurality of user attributes using the machine learning model; and refining the machine learning model based on a difference between the predicted outcome score and the outcome score.

5. A method, comprising:

generating an outcome score by processing service data describing a healthcare service plan for a historical user, wherein the outcome score is based at least in part on whether the historical user was hospitalized while on the healthcare service plan, comprising:

determining, based on the service data, that the historical user was hospitalized while on the healthcare service plan;

determining, based on the service data, an amount of time that elapsed between a start of the healthcare service plan and a time when the historical user was hospitalized; and computing the outcome score based at least in part on the amount of time;

training a machine learning model to evaluate healthcare service plans based on the outcome score;

receiving user data describing one or more conditions of a user for a first window of time;

generating a first healthcare service plan for the user, comprising:

extracting a first plurality of user attributes, from the user data, for the user;

generating a first alternative healthcare service plan by selecting a set of home healthcare services, from a plurality of alternative healthcare services, to be provided to the user in a residence of the user;

generating a first predicted outcome score by processing the set of home healthcare services and the first plurality of user attributes using a trained machine learning model, wherein the first predicted outcome score indicates a probability of future hospitalization, during a second window of time subsequent to the first window of time, if the set of home healthcare services are provided to the user in the residence of the user;

generating a plurality of predicted outcome scores by processing a plurality of alternate healthcare service plans using the trained machine learning model; and selecting the first healthcare service plan based on determining that the first predicted outcome score is greater than each of the plurality of predicted outcome scores; and implementing the first healthcare service plan for the user based at least in part on the first predicted outcome score, wherein after the implementation, the set of home healthcare services are provided to the user in the residence of the user.

6. The method of claim 5, wherein implementing the first healthcare service plan comprises:

outputting the first healthcare service plan to a healthcare provider;

receiving approval, from the healthcare provider, of the first healthcare service plan;

determining a calendar of the user; and for each respective home healthcare service in the first healthcare service plan:

identifying a respective servicer to provide the respective home healthcare service; and scheduling the respective servicer to provide the respective home healthcare service based on the calendar of the user.

7. The method of claim 6, wherein outputting the first healthcare service plan comprises displaying the set of home healthcare services and the first predicted outcome score on a graphical user interface (GUI).

8. The method of claim 5, wherein the first healthcare service plan comprises at least one of:

one or more home modifications, remote monitoring, emergency call equipment, dietician assistance, one or more therapies, or in-home assistance from a healthcare provider.

9. The method of claim 8, wherein the first healthcare service plan enables the user to reside at home with reduced risk of harm or hospitalization, as compared to at least a second healthcare service plan having a different set of home healthcare services.

10. The method of claim 5, further comprising:

determining whether the user was hospitalized while on the first healthcare service plan; and refining the trained machine learning model based on whether the user was hospitalized.

11. The method of claim 10, further comprising:

identifying a third party associated with the user, wherein the third party comprises at least one of: a referral source of the user, a payer for the first healthcare service plan, or a previous healthcare provider of the user; and automatically transmitting, to the third party, an indication of whether the user was hospitalized while on the first healthcare service plan.

12. The method of claim 5, further comprising, upon determining that at least one of the first plurality of user attributes changed after the first healthcare service plan was implemented:

extracting a new plurality of user attributes for the user;

selecting a new healthcare service plan; and generating a new predicted outcome score by processing the new healthcare service plan and the new plurality of user attributes using the trained machine learning model.

13. A non-transitory computer-readable storage medium comprising computer-readable program code that, when executed using one or more computer processors, performs an operation comprising:

generating an outcome score by processing service data describing a healthcare service plan for a historical user, wherein the outcome score is based at least in part on whether the historical user was hospitalized while on the healthcare service plan, comprising:

determining, based on the service data, that the historical user was hospitalized while on the healthcare service plan;

determining, based on the service data, an amount of time that elapsed between a start of the healthcare service plan and a time when the historical user was hospitalized; and computing the outcome score based at least in part on the amount of time;

training a machine learning model to evaluate healthcare service plans based on the outcome score;

receiving user data describing one or more conditions of a user for a first window of time;

generating a first healthcare service plan for the user, comprising:

extracting a first plurality of user attributes, from the user data, for the user;

generating a first alternative healthcare service plan by selecting a set of home healthcare services, from a plurality of alternative healthcare services, to be provided to the user in a residence of the user;

generating a first predicted outcome score by processing the set of home healthcare services and the first plurality of user attributes using a trained machine learning model, wherein the first predicted outcome score indicates a probability of future hospitalization, during a second window of time subsequent to the first window of time, if the set of home healthcare services are provided to the user in the residence of the user;

generating a plurality of predicted outcome scores by processing a plurality of alternate healthcare service plans using the trained machine learning model; and selecting the first healthcare service plan based on determining that the first predicted outcome score is greater than each of the plurality of predicted outcome scores; and implementing the first healthcare service plan for the user based at least in part on the first predicted outcome score, wherein after the implementation, the set of one or more home healthcare services are provided to the user in the residence of the user.

14. The non-transitory computer-readable storage medium of claim 13, wherein implementing the first healthcare service plan comprises:

displaying the set of home healthcare services and the first predicted outcome score on a graphical user interface (GUI);

receiving approval, from a healthcare provider, of the first healthcare service plan;

determining a calendar of the user; and for each respective home healthcare service in the first healthcare service plan:

identifying a respective servicer to provide the respective home healthcare service; and scheduling the respective servicer to provide the respective home healthcare service based on the calendar of the user.

15. The non-transitory computer-readable storage medium of claim 13, wherein the first healthcare service plan comprises at least one of:

one or more home modifications, remote monitoring, emergency call equipment, dietician assistance, one or more therapies, or in-home assistance from a healthcare provider.

16. The non-transitory computer-readable storage medium of claim 13, the operation further comprising:

determining whether the user was hospitalized while on the first healthcare service plan; and refining the trained machine learning model based on whether the user was hospitalized.

17. The non-transitory computer-readable storage medium of claim 16, the operation further comprising:

identifying a third party associated with the user, wherein the third party comprises at least one of: a referral source of the user, a payer for the first healthcare service plan, or a previous healthcare provider of the user; and automatically transmitting, to the third party, an indication of whether the user was hospitalized while on the first healthcare service plan.

\* \* \* \* \*